(12) United States Patent
Skead et al.

(10) Patent No.: US 6,951,943 B2
(45) Date of Patent: Oct. 4, 2005

(54) PROCESS FOR THE PREPARATION OF PHENYLALANINE ENAMIDE DERIVATIVES

(75) Inventors: Benjamin Mark Skead, Fulbourn (GB); Nicholas David Tyrrell, Cambridge (GB); Stephen Wilfred Jones, Ely (GB); Michael Handforth Brookes, Cambridge (GB)

(73) Assignee: Celltech R & D Limited, Slough (GB)

(*) Notice: Subject to any disclaimer, the term of this patent is extended or adjusted under 35 U.S.C. 154(b) by 0 days.

(21) Appl. No.: 10/620,396

(22) Filed: Jul. 16, 2003

(65) Prior Publication Data

US 2004/0073033 A1 Apr. 15, 2004

(30) Foreign Application Priority Data

Jul. 17, 2002 (EP) ................................. 0216574

(51) Int. Cl.⁷ ....................... C07D 471/04; C07D 213/72
(52) U.S. Cl. ........................ 546/122; 546/304; 549/331; 560/21; 562/457
(58) Field of Search ................. 546/122, 304; 560/21; 562/457; 549/331

(56) References Cited

FOREIGN PATENT DOCUMENTS

WO  WO 02/068393  *  9/2002  ......... C07D/213/81

OTHER PUBLICATIONS

Dunn, A.D., "The reaction of some brominated aminopicolines with acetic anhydride and with copper(I) cyanide," *J. Prakt. Chem.*, 1996, 338, 663–666.
Fieser, et al., Reagents for Organic Synthesis, *John Wiley & Sons*, 1999, vols. 1–19.
Katritzky (Ed.), Comprehensive Heterocyclic Chemistry, *Pergamon*, 1984, vols. 1–8.
Katritzky (Ed.), Comprehensive Heterocyclic Chemistry, *Pergamon*, 1994, vols. 1–11.
Katritzky, (Ed.), Comprehensive Organic Functional Group Transformations, *Pergamon*, 1995, vols. 1–7.
Larocks's comprehensive Organic Transformations, *VCH Publishers, Inc.*, 1989.
March's Advanced Organic Chemistry, *John Wiley & Sons*, 1992.
Paquette (Ed.), Encyclopedia of Reagents for Organic Synthesis, *John Wiley & Sons*, 1995, vols. 1–8.
Rodd's Chemistry of Carbon Compounds, *Elsevier Science Publishers*, 1989, vols. 1–15.
Trost, et al. (Eds.), Comprehensive Organic Synthesis, *Pergamon*, 1991, vols. 1–9.
Wasserman, H.H., et al., "Cyclobutenone derivatives from ethoxyacetylene," *J. Org. Chem.*, 1973, 38(8), 1451–1455.

* cited by examiner

Primary Examiner—Charanjit S. Aulakh
(74) Attorney, Agent, or Firm—Woodcock Washburn LLP

(57) ABSTRACT

A process for the preparation of a class of phenylalanine enamide derivatives is described:

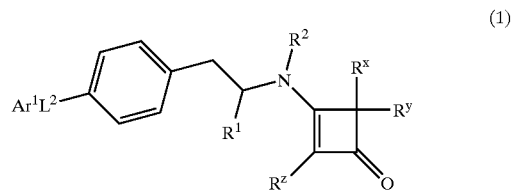

(1)

wherein:
$Ar^1$ is an optionally substituted aromatic or heteroaromatic group; $L^2$ is a linker group selected from $-N(R^4)-$ [where $R^4$ is a hydrogen atom or an optionally substituted straight or branched $C_{1-6}$alkyl group], $-CON(R^4)-$, or $-S(O)_2N(R^4)-$;
$R^1$ is a carboxylic acid ($-CO_2H$) or a derivative or biostere thereof; $R^2$ is a hydrogen atom or a $C_{1-6}$alkyl group; $R^x$, $R^y$ and $R^z$ which may be the same or different is each an atom or group $-L^1(Alk^1)_n(R^3)_v$;
and the salts, solvates, hydrates and N-oxides thereof;
which comprises reacting a compound of formula (2):

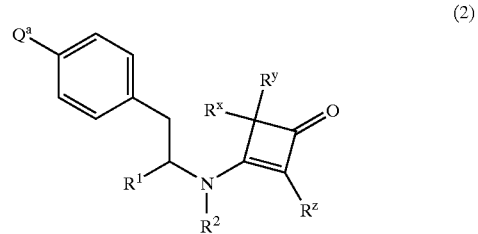

(2)

wherein:
$Q^a$ is a group $-N(R^4)H$;
and the salts, solvates, hydrates and N-oxides thereof;
with a compound $Ar^1W$ wherein W is a group selected from $X^1$(wherein $X^1$ is a leaving atom or group), $-COX^2$ (wherein $X^2$ is a halogen atom or a $-OH$ group) or $-SO_2X^3$ (in which $X^3$ is a halogen atom).

27 Claims, No Drawings

PROCESS FOR THE PREPARATION OF PHENYLALANINE ENAMIDE DERIVATIVES

This application claims the benefit under 35 U.S.C. § 119 (a)–(d) of United Kingdom Application No. GB 0216574.4, filed Jul. 17, 2002, which is incorporated herein by reference in its entirety.

The present invention relates to processes and intermediates for the synthesis of a class of phenylalanine enamide derivatives, the final products being useful as α4 integrin inhibitors.

The role of α4 integrin inhibitors, such as α4β7 and/or α4β1 inhibitors, for use in medicine is discussed, for example, in International Patent Application Number WO 02/068,393.

We have now developed a process for the production of a class of α4 integrin inhibitors, as defined hereinafter, which is particularly amenable for the large scale synthesis of the compounds. The process is simple to operate and advantageously limits the need to use protecting groups.

Thus according to one aspect of the invention we provide a process for the preparation of phenylalanine enamide derivatives of the general formula (1):

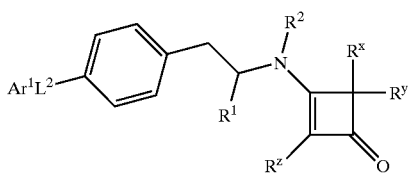

(1)

wherein:

$Ar^1$ is an optionally substituted aromatic or heteroaromatic group;

$L^2$ is a linker group selected from —N($R^4$)—[where $R^4$ is a hydrogen atom or an optionally substituted straight or branched $C_{1-6}$alkyl group], —CON($R^4$)—, or —S(O)$_2$N($R^4$)—;

$R^1$ is a carboxylic acid (—CO$_2$H) or a derivative or biostere thereof;

$R^2$ is a hydrogen atom or a $C_{1-6}$alkyl group;

$R^x$, $R^y$ and $R^z$ which may be the same or different is each an atom or group -$L^1$(Alk$^1$)$_n$($R^3$)$_v$ in which $L^1$ is a covalent bond or a linker atom or group, Alk$^1$ is an optionally substituted aliphatic or heteroaliphatic chain, $R^3$ is a hydrogen or halogen atom or group selected from —OR$^{3a}$ [where $R^{3a}$ is a hydrogen atom or an optionally substituted straight or branched $C_{1-6}$alkyl group or $C_{3-8}$cycloalkyl group], —SR$^{3a}$, —CN or an optionally substituted cycloaliphatic, heterocycloaliphatic, polycycloaliphatic, heteropolycycloaliphatic, aromatic or heteroaromatic group, n is zero or the integer 1 and v is the integer 1, 2 or 3 provided that when n is zero and $L^1$ is a covalent bond v is the integer 1; or $R^z$ is an atom or group as previously defined and $R^x$ and $R^y$ are joined together to form an optionally substituted spiro linked cycloaliphatic or heterocycloaliphatic group;

and the salts, solvates, hydrates and N-oxides thereof; which comprises reacting a compound of formula (2):

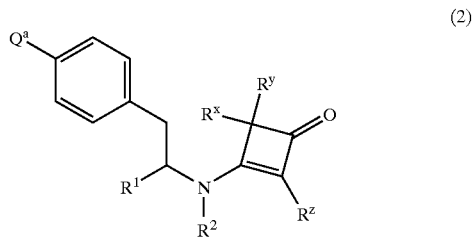

(2)

wherein:
$Q^a$ is a group —N($R^4$)H;
and the salts, solvates, hydrates and N-oxides thereof;
with a compound Ar$^1$W wherein W is a group selected from $X^1$ (wherein $X^1$ is a leaving atom or group such as a halogen atom, e.g. a fluorine, bromine, iodine or chlorine atom or a sulfonyloxy group such as an alkylsulfonyloxy, e.g. trifluoro-methylsulfonyloxy or arylsulfonyloxy, e.g. p-toluenesulfonyloxy group), —COX$^2$ (wherein $X^2$ is a halogen atom such as a chlorine atom or a —OH group) or —SO$_2$X$^3$ (in which $X^3$ is a halogen atom such as chlorine).

It will be appreciated that compounds of formulae (1), (2) or Ar$^1$W may have one or more chiral centres, and exist as enantiomers or diastereomers. The process is to be understood to extend to all such enantiomers, diastereomers and mixtures thereof, including racemates. Formulae (1), (2) or Ar$^1$W and the formulae hereinafter are intended to represent all individual isomers and mixtures thereof, unless stated or shown otherwise. In addition, compounds of formulae (1), (2) or Ar$^1$W may exist as tautomers, for example keto (CH$_2$C=O)-enol (CH=CHOH) tautomers. Formulae (1), (2) or Ar$^1$W and the formulae hereinafter are intended to represent all individual tautomers and mixtures thereof, unless stated otherwise.

In the compounds described herein optionally substituted aromatic groups which may be represented by the group Ar$^1$ include for example optionally substituted monocyclic or bicyclic fused ring $C_{6-12}$aromatic groups, such as phenyl, 1- or 2-naphthyl, 1- or 2-tetrahydronaphthyl, indanyl or indenyl groups.

Optionally substituted heteroaromatic groups which may be represented by the group Ar$^1$ include for example optionally substituted $C_{1-9}$heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—C$_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, e.g. 2,6-naphthyridinyl, or 2,7-naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl, 5,6,7,8-tetrahydro-isoquinolinyl, and imidyl, e.g. succinimidyl, phthalimidyl, or naphthalimidyl such as 1,8-naphthalimidyl.

Each aromatic or heteroaromatic group represented by the group $Ar^1$ may be optionally substituted on any available carbon or, when present, nitrogen atom. One, two, three or more of the same or different substituents may be present and each substituent may be selected for example from an atom or group $-L^3(Alk^2)_t L^4(R^5)_u$ in which $L^3$ and $L^4$, which may be the same or different, is each a covalent bond or a linker atom or group, t is zero or the integer 1, u is an integer 1, 2 or 3, $Alk^2$ is an optionally substituted aliphatic or heteroaliphatic chain and $R^5$ is a hydrogen or halogen atom or a group selected from optionally substituted $C_{1-6}$alkyl or $C_{3-8}$cycloalkyl, $-OR^6$ [where $R^6$ is a hydrogen atom, an optionally substitued $C_{1-6}$alkyl or $C_{3-8}$cycloalkyl group], $-SR^6$, $-NR^6R^7$ [where $R^7$ is as just defined for $R^6$ and may be the same or different], $-NO_2$, $-CN$, $-CO_2R^6$, $-SO_3H$, $-SOR^6$, $-SO_2R^6$, $-SO_3R^6$, $-OCO_2R^6$, $-CONR^6R^7$, $-OCONR^6R^7$, $-CSNR^6R^7$, $-COR^6$, $-OCOR^6$, $-N(R^6)COR^7$, $-N(R^6)CSR^7$, $-SO_2N(R^6)(R^7)$, $-N(R^6)SO_2R^7$, $N(R^6)CON(R^7)(R^8)$ [where $R^8$ is a hydrogen atom, an optionally substituted $C_{1-6}$alkyl or $C_{3-8}$cycloalkyl group], $-N(R^6)CSN(R^7)(R^8)$ or $-N(R^6)SO_2N(R^7)(R^8)$, provided that when t is zero and each of $L^3$ and $L^4$ is a covalent bond then u is the integer 1 and $R^5$ is other than a hydrogen atom.

When $L^3$ and/or $L^4$ is present in these substituents as a linker atom or group it may be any divalent linking atom or group. Particular examples include $-O-$ or $-S-$ atoms or $-C(O)-$, $-C(O)O-$, $-OC(O)-$, $-C(S)-$, $-S(O)-$, $-S(O)_2-$, $-N(R^8)-$ [where $R^8$ is a hydrogen atom or an optionally substituted straight or branched $C_{1-6}$alkyl group], $-CON(R^8)-$, $-OC(O)N(R^8)-$, $-CSN(R^8)-$, $-N(R^8)CO-$, $-N(R^8)C(O)O-$, $-N(R^8)CS-$, $-S(O)_2N(R^8)-$, $-N(R^8)S(O)_2-$, $-N(R^8)O-$, $-ON(R^8)-$, $-N(R^8)N(R^8)-$, $-N(R^8)CON(R^8)-$, $-N(R^8)CSN(R^8)-$, or $-N(R^8)SO_2N(R^8)-$ groups.

Where the linker group contains two $R^8$ substituents, these may be the same or different.

When $R^{3a}$, $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl, ethyl or i-propyl group. $C_{3-8}$cycloalkyl groups represented by $R^{3a}$, $R^5$, $R^6$, $R^7$ and/or $R^8$ include $C_{3-8}$cycloalkyl groups e.g. cyclopropyl, cyclobutyl, cyclopentyl and cyclohexyl groups. Optional substituents which may be present on such alkyl or cycloalkyl groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^6$ and $R^7$ or $R^7$ and $R^8$ are both $C_{1-6}$alkyl groups these groups may be joined, together with the N atom to which they are attached, to form a heterocyclic ring. Such heterocyclic rings may be optionally interrupted by a further heteroatom selected from $-O-$, $-S-$ or $-N(R^6)-$. Particular examples of such heterocyclic rings include piperidinyl, morpholinyl, thiomorpholinyl, pyrrolidinyl, imidazolidinyl and piperazinyl rings.

When $Alk^2$ is present as an optionally substituted aliphatic or heteroaliphatic chain it may be any optionally substituted aliphatic or heteroaliphatic chain as described hereinafter for $Alk^1$.

Halogen atoms represented by $R^5$ in the optional $Ar^1$ substituents include fluorine, chlorine, bromine, or iodine atoms.

Examples of the substituents represented by $-L^3(Alk^2)_t L^4(R^5)_u$ when present in $Ar^1$ groups in compounds of formulae (1) or (iii) include atoms or groups $-L^3 Alk^2 L^4 R^5$, $-L^3 Alk^2 R^5$, $-L^3 R^5$, $-R^5$ and $-Alk^2 R^5$ wherein $L^3$, $Alk^2$, $L^4$ and $R^5$ are as defined above. Particular examples of such substituents include $-L^3CH_2L^4R^5$, $-L^3CH(CH_3)L^4R^5$, $-L^3(CH_2)_2L^4R^5$, $-L^3CH_2R^5$, $-L^3CH(CH_3)R^5$, $-L^3(CH_2)_2R^5$, $-CH_2R^5$, $-CH(CH_3)R^5$, $-(CH_2)_2R^5$ and $-R^5$ groups.

Thus $Ar^1$ in compounds of formulae (1) or $Ar^1W$ may be optionally substituted for example by one, two, three or more halogen atoms, e.g. fluorine, chlorine, bromine or iodine atoms, and/or $C_{1-6}$alkyl, e.g. methyl, ethyl, n-propyl, i-propyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or $-C(OH)(CF_3)_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. $-CF_3$, $-CHF_2$, $-CH_2F$, halo$C_{1-6}$alkoxy, e.g. $-OCF_3$, $-OCHF_2$, $-OCH_2F$, $C_{1-6}$alkylamino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylamino-ethoxy, $C_{1-6}$dialkylamino$C_{1-6}$alkoxy, e.g. dimethylaminoethoxy, diethyl-aminoethoxy, diisopropylaminoethoxy or dimethylaminopropoxy, nitro, cyano, amidino, hydroxyl ($-OH$), formyl [HC(O)$-$], carboxyl ($-CO_2H$), $-CO_2R^6$ e.g. $-CO_2CH_3$ or $-CO_2C(CH_3)_3$, $C_{1-6}$alkanoyl e.g. acetyl, thiol ($-SH$), thio$C_{1-6}$alkyl, e.g. thiomethyl or thioethyl, sulphonyl ($-SO_3H$), $-SO_3R^6$, $C_{1-6}$alkylsulphinyl, e.g. methylsulphinyl, $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido ($-CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$alkylamino$C_{1-6}$alkylaminocarbonyl, e.g. ethylaminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethyl-amino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkyl-amino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, C$_{1-6}$alkanoylamino, e.g. acetylamino, aminoC$_{1-6}$ alkanoylamino e.g. aminoacetylamino, C$_{1-6}$dialkylaminoC$_{1-6}$ alkanoyl-amino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino groups.

When the group R$^2$ is present in compounds of formulae (1) or (2) as a C$_{1-6}$alkyl group it may be for example a straight or branched C$_{1-6}$alkyl group e.g. a C$_{1-3}$alkyl group such as a methyl or ethyl group.

When the group R$^1$ in compounds of formulae (1) or (2) is present as a derivative of a carboxylic acid it may be for example an acyclic or cyclic carboxylic acid ester or an amide. Particular acyclic esters and amides include —CO$_2$Alk$^7$ and —CONR$^6$R$^7$ groups as defined herein. When R$^1$ is a biostere of a carboxylic acid it may be for example a tetrazole or other acid such as phosphonic acid, phosphinic acid, sulphonic acid, sulphinic acid or boronic acid or an acylsulphonamide group.

Esterified carboxyl groups represented by the group —CO$_2$Alk$^7$ include groups wherein Alk$^7$ is a straight or branched optionally substituted C$_{1-8}$alkyl group such as a methyl, ethyl, n-propyl, i-propyl, n-butyl, i-butyl, s-butyl, t-butyl, pentyl or neopentyl group; an optionally substituted C$_{2-8}$alkenyl group such as a propenyl e.g. 2-propenyl or butenyl e.g. 2-butenyl or 3-butenyl group, an optionally substituted C$_{2-8}$alkynyl group such as a ethynyl, propynyl e.g. 2-propynyl or butynyl e.g. 2-butynyl or 3-butynyl group, an optionally substituted C$_{3-8}$cycloalkyl group such as a cyclopropyl, cyclobutyl, cyclopentyl, cyclohexyl or cycloheptyl group; an optionally substituted C$_{3-8}$heterocycloalkyl group such as a tetrahydrofuranyl e.g. tetrahydrofuran-3-yl, pyrrolidinyl e.g. 1-methylpyrrolidinyl such as 1-methylpyrrolidin-3-yl, piperidinyl e.g. 1-methylpiperidinyl such as 1-methylpiperidin-4-yl, tetrahydropyranyl e.g. tetrahydropyran-4-yl or 2-oxo-[1,3]dioxol-4-yl e.g. 5-methyl-2-oxo-[1,3]dioxol-4-yl group; an optionally substituted C$_{3-8}$cycloalkylC$_{1-8}$alkyl group such as a cyclopentylmethyl, cyclohexylmethyl, or cyclohexylethyl group; an optionally substituted C$_{3-8}$heterocycloalkylC$_{1-8}$alkyl group such as a morpholinyl-N-ethyl, thiomorpholinyl-N-methyl, pyrrolidinyl-N-ethyl, pyrrolidinyl-N-propyl, piperidinyl-N-ethyl, pyrazolidinyl-N-methyl or piperazinyl-N-ethyl group; an optionally substituted C$_{1-6}$alkyloxyC$_{1-6}$alkyl group such as a methyloxyethyl or propyloxyethyl group; an optionally substituted hydroxyC$_{1-6}$alkyl group such as a hydroxyethyl e.g. 2-hydroxyethyl or hydroxypropyl e.g. 2-hydroxypropyl, 3-hydroxypropyl or 2,3-dihydroxypropyl group; an optionally substituted C$_{1-6}$alkylthioC$_{1-6}$alkyl group such as an ethylthioethyl group; an optionally substituted C$_{1-6}$alkylsulfinylC$_{1-6}$alkyl group such as an methylsulfinylethyl group; an optionally substituted C$_{1-6}$alkylsulfonylC$_{1-6}$alkyl group such as an methylsulfonylmethyl group; an optionally substituted C$_{3-8}$cycloalkyloxyC1-6alkyl group such as a cyclohexyloxymethyl group; an optionally substituted C$_{3-8}$cycloalkylthioC$_{1-6}$alkyl group such as cyclopentylthiomethyl group; an optionally substituted C$_{3-8}$cycloalkylsulfinylC$_{1-6}$alkyl group such as a cyclopentyl-sulfinylmethyl group; an optionally substituted C$_{3-8}$cycloalkylsulfonylC$_{1-6}$alkyl group such as a cyclopentylsulfonylmethyl group; an optionally substituted C$_{1-6}$alkyloxycarbonylC$_{1-6}$alkyl group such as isobutoxycarbonylpropyl group; an optionally substituted C$_{1-6}$alkyloxycarbonylC$_{1-6}$alkenyl group such as isobutoxycarbonylpentenyl group; an optionally substituted C$_{1-6}$alkyloxycarbonyloxyC$_{1-6}$alkyl group such as an ethyloxycarbonyloxymethyl or isopropoxycarbonyloxyethyl e.g. 1-(isopropoxycarbonyloxy)ethyl or 2-(isopropoxycarbonyloxy)ethyl group; an optionally substituted C$_{1-6}$alkyloxycarbonyloxyC$_{1-6}$alkenyl group such as a isopropoxycarbonyloxybutenyl group, an optionally substituted C$_{3-8}$cycloalkyloxycarbonyloxyC$_{1-6}$alkyl group such as a cyclohexyloxycarbonyloxyethyl, e.g. a 2-(cyclohexyloxycarbonyloxy)ethyl group, an optionally substituted N-di-C$_{1-8}$alkylaminoC$_{1-8}$alkyl group such as a N-dimethylaminoethyl or N-diethylaminoethyl group; an optionally substituted N—C$_{6-12}$aryl-N—C$_{1-6}$alkylaminoC$_{1-6}$alkyl group such as a N-phenyl-N-methylaminomethyl group; an optionally substituted N-di-C$_{1-8}$alkylcarbamoylC$_{1-8}$alkyl group such as a N-diethylcarbamoylmethyl group; an optionally substituted C$_{6-12}$arylC$_{1-6}$alkyl group such as an optionally substituted benzyl, phenylethyl, phenylpropyl, 1-naphthylmethyl or 2-naphthylmethyl group; an optionally substituted heteroC$_{6-10}$arylC$_{1-6}$alkyl group, such as a pyridinylmethyl e.g. pyridin-4-ylmethyl or imidazolylethyl e.g. 2-imidazol-1-ylethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; a C$_{6-12}$arylthioC$_{1-8}$alkyl group such as an optionally substituted phenylthioethyl group; a C$_{6-12}$arylsulfinylC$_{1-8}$alkyl group such as an optionally substituted phenylsulfinylmethyl group; a C$_{6-12}$arylsulfonylC$_{1-8}$alkyl group such as an optionally substituted phenylsulfonylmethyl group; an optionally substituted C$_{1-8}$alkanoyloxyC$_{1-8}$alkyl group, such as a acetoxymethyl, ethoxycarbonyloxyethyl, pivaloyloxymethyl, propionyloxyethyl or propionyloxypropyl group; an optionally substituted C$_{4-8}$imidoC$_{1-8}$alkyl group such as a succinimidomethyl or phthalamidoethyl group; a C$_{6-12}$aroyloxyC$_{1-8}$alkyl group such as an optionally substituted benzoyloxyethyl or benzoyloxypropyl group or a triglyceride such as a 2-substituted triglyceride e.g. a 1,3-di-C$_{1-8}$alkylglycerol-2-yl group such as a 1,3-diheptylglycerol-2-yl group. Optional substituents present on the Alk$^7$ group include R$^{13a}$ substituents described below.

It will be appreciated that in the forgoing list of Alk$^7$ groups the point of attachment to the remainder of the compounds of formulae (1) or (2) is via the last described part of the Alk$^7$ group. Thus, for example a methoxyethyl group would be attached by the ethyl group, whilst a morpholinyl-N-ethyl group would be attached via the N-ethyl group.

It will be further appreciated that in the forgoing list of Alk$^7$ groups, where not specifically mentioned, alkyl groups may be replaced by alkenyl or alkynyl groups where such groups are as previously defined for Alk$^1$. Additionally these alkyl, alkenyl or alkynyl groups may optionally be interrupted by one, two or three linker atoms or groups where such linker atoms and groups are as previously defined for L$^3$.

Further, prodrugs of compounds of formula (1) which may be prepared using the process of the invention include cyclic esters where X is a —N(R$^2$)— group in which R$^2$ becomes a C$_{1-6}$alkyl joining chain, especially a —CH$_2$— or —CH₂CH₂— chain, which is also connected to the acid group R¹ to form a cyclic ester of formula (1a):

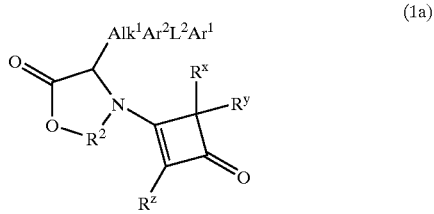

(1a)

When present in the group $R^x$, $R^y$ and/or $R^z$ in compounds of formulae (1) or (2) the linker atom or group represented by $L^1$ may be any linker atom or group as described above for the linker atom or group $L^3$. In addition $L^1$ may also be a —Se— atom.

When $Alk^1$ is present in the group $R^x$, $R^y$ and/or $R^z$ in compounds of formulae (1) or (2) as an optionally substituted aliphatic chain it may be an optionally substituted $C_{1-10}$ aliphatic chain. Particular examples include optionally substituted straight or branched chain $C_{1-6}$alkylene, $C_{2-6}$alkenylene or $C_{2-6}$alkynylene chains.

Particular examples of aliphatic chains represented by $Alk^1$ include optionally substituted —CH₂—, —(CH₂)₂—, —CH(CH₃)CH₂—, —(CH₂)₂CH₂—, —(CH₂)₃CH₂—, —CH(CH₃)(CH₂)₂—, —CH₂CH(CH₃)CH₂—, —C(CH₃)₂CH₂—, —CH₂C(CH₃)₂CH₂—, —(CH₂)₂C(CH₃)₂CH₂—, —(CH₂)₄CH₂—, —(CH₂)₅CH₂—, —CHCH—, —CHCHCH₂—, —CH₂CHCH—, —CHCHCH₂CH₂—, —CH₂CHCHCH₂—, —(CH₂)₂CHCH—, —CC—, —CCCH₂—, —CH₂CC—, —CCCH₂CH₂—, —CH₂CCCH₂— or —(CH₂)₂CC— chains.

Heteroaliphatic chains represented by $Alk^1$ when present in the group $R^x$, $R^y$ and/or $R^z$ in compounds of formulae (1) or (2) include the aliphatic chains just described for $Alk^1$ but with each additionally containing one, two, three or four heteroatoms or heteroatom-containing groups. Particular hetero-atoms or groups include atoms or groups $L^5$ where $L^5$ is as defined above for $L^3$ when $L^3$ is a linker atom or group. Each $L^5$ atom or group may interrupt the aliphatic chain, or may be positioned at its terminal carbon atom to connect the chain to an adjoining atom or group. Particular examples include optionally substituted —CH₂L⁵—, —CH₂CH₂L⁵—, -L⁵CH₂—, -L⁵CH₂CH₂—, -L⁵CH(CH₃)CH₂—, -L⁵CH₂CH(CH₃)CH₂—, -L⁵CH₂CH₂CH(CH₃)—, -L⁵C(CH₃)₂CH₂—, —CH₂L⁵CH₂CH₂—, —(CH₂)₂L⁵CH₂—, —(CH₂)₃L⁵CH₂—, -L⁵(CH₂)₃—, -L⁵(CH₂)₄—, —CH₂L⁵CH₂CHL⁵CH₂— and —(CH₂)₂L⁵CH₂CH₂— chains.

The optional substituents which may be present on aliphatic or heteroaliphatic chains represented by $Alk^1$ include one, two, three or more substituents where each substituent may be the same or different and is selected from halogen atoms, e.g. fluorine, chlorine, bromine or iodine atoms, or —OH, —CO₂H, —CO₂R⁹, where R⁹ is an optionally substituted straight or branched $C_{1-6}$alkyl group as defined above for R⁵, —CONHR⁹, —CON(R⁹)₂, —COR⁹, e.g. —COCH₃, $C_{1-6}$alkoxy, e.g. methoxy or ethoxy, thiol, —S(O)R⁹, —S(O)₂R⁹, $C_{1-6}$alkylthio e.g. methylthio or ethylthio, amino or substituted amino groups. Substituted amino groups include —NHR⁹ and —N(R⁹)₂ groups. Where two R⁹ groups are present in any of the above substituents these may be the same or different.

Optionally substituted cycloaliphatic groups represented by the group R³ when present in the group $R^x$, $R^y$ and/or $R^z$ in compounds of the invention include optionally substituted $C_{3-10}$cycloaliphatic groups. Particular examples include optionally substituted $C_{3-10}$cycloalkyl, e.g. $C_{3-8}$cycloalkyl or $C_{3-10}$cycloalkenyl, e.g $C_{3-8}$cycloalkenyl groups.

Optionally substituted heterocycloaliphatic groups represented by the group R³ when present in the group $R^x$, $R^y$ and/or $R^z$ include optionally substituted $C_{3-10}$heterocycloaliphatic groups. Particular examples include optionally substituted $C_{3-10}$heterocycloalkyl, e.g. $C_{3-7}$heterocycloalkyl, or $C_{3-10}$heterocycloalkenyl, e.g. $C_{3-7}$hetercycloalkenyl groups, each of said groups containing one, two, three or four heteroatoms or heteroatom-containing groups $L^5$ as defined above.

Optionally substituted polycycloaliphatic groups represented by the group R³ when present in the group $R^x$, $R^y$ and/or $R^z$ include optionally substitued $C_{7-10}$bi- or tricycloalkyl or $C_{7-10}$bi- or tricycloalkenyl groups. Optionally substituted heteropolycycloaliphatic groups represented by the group R³ include the optionally substituted polycycloaliphatic groups just described, but with each group additionally containing one, two, three or four $L^5$ atoms or groups.

Particular examples of cycloaliphatic, polycycloaliphatic, heterocyclo-aliphatic and heteropolycycloaliphatic groups represented by the group R³ include optionally substituted cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl, 2-cyclobuten-1-yl, 2-cyclopenten-1-yl, 3-cyclopenten-1-yl, adamantyl, norbornyl, norbornenyl, tetrahydrofuranyl, tetrahydrothiophenyl, tetrahydrothiophene-1-oxide, tetrahydrothiophene-1,1-dioxide, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, tetrahydropyranyl, tetrahydrothiopyranyl, tetrahydrothiopyran-1-oxide, tetrahydrothiopyran-1,1-dioxide, piperidinyl, piperidinone, dioxanyl e.g. 1,3-dioxanyl or 1,4-dioxanyl, morpholinyl, morpholinone, dithianyl, e.g. 1,3-dithianyl or 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or heteropolycycloaliphatic groups represented by the group R³ include one, two, three or more substituents each selected from halogen atoms, e.g. fluorine, chlorine, bromine or iodine atoms, or $C_{1-6}$alkyl, e.g. methyl, ethyl, propyl or i-propyl, halo$C_{1-6}$alkyl, e.g. halomethyl or haloethyl such as difluoromethyl or trifluoromethyl, optionally substituted by hydroxyl, e.g. —C(OH)(CF₃)₂, $C_{1-6}$alkoxy, e.g. methoxy, ethoxy or propoxy, halo$C_{1-6}$alkoxy, e.g. halomethoxy or haloethoxy such as difluoromethoxy or trifluoromethoxy, thiol, $C_{1-6}$alkylthio e.g. methylthio, ethylthio or propylthio, or -(Alk⁴)$_g$R¹⁰ groups in which Alk⁴ is a straight or branched $C_{1-3}$alkylene chain, g is zero or an integer 1 and R¹⁰ is a —OH, —SH, —N(R¹¹)₂, (in which R¹¹ is an atom or group as defined herein for R⁸) —CN, —CO₂R¹¹, —NO₂, —CON(R¹¹)₂, —CSN(R¹¹)₂, —COR¹¹, —CSN(R¹¹)₂, —N(R¹¹)COR¹¹, —N(R¹¹)CSR¹¹, —SO₂N(R¹¹)₂, —N(R¹¹)SO₂R¹¹, —N(R¹¹)CON(R¹¹)₂, —N(R¹¹)CSN(R¹¹), N(R¹¹)SO₂N(R¹¹)₂ or optionally substituted phenyl group. Where two R¹¹ atoms or groups are present in these substituents these may be the same or different or joined to form a heterocyclic ring as previously described when $R^6$ and $R^7$ are joined together. Optionally substituted phenyl groups include phenyl substituted by one, two or three of the $R^{13}$ groups described below.

Additionally, when the group $R^3$ is a heterocycloaliphatic group containing one or more nitrogen atoms each nitrogen atom may be optionally substituted by a group -$(L^6)_p(Alk^5)_q$ $R^{12}$ in which $L^6$ is —C(O)—, —C(O)O—, —C(S)—, —S(O)$_2$—, —CON($R^8$)—, —CSN($R^8$)— or SO$_2$N($R^8$)—; p is zero or an integer 1; Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

$C_{1-3}$alkylene chains represented by Alk$^4$ include —CH$_2$—, —CH$_2$CH$_2$—, —CH$_2$CH$_2$CH$_2$—, —CH(CH$_3$)CH$_2$— and —CH$_2$CH(CH$_3$)— chains.

Optionally substituted aliphatic or heteroaliphatic chains represented by Alk$^5$ include those optionally substituted chains described above for Alk$^1$. Optional substituents which may be present on these groups include those described above in relation to Alk$^1$.

Cycloaliphatic, heterocycloaliphatic, polycycloaliphatic or polyheterocycloaliphatic groups represented by $R^{12}$ include those groups just described for the group $R^3$. Optional substituents which may be present on those groups include those described above in relation to $R^3$ cycloaliphatic groups.

Aromatic or heteroaromatic groups represented by $R^{12}$ include those groups described herein for the group Ar$^1$. Optional substituents which may be present on these groups include those $R^{13}$ optional substituents described hereinafter.

When the group $R^3$ is an optionally substituted aromatic or heteroaromatic group it may be for example an aromatic or heteroaromatic group as described herein for the group Ar$^1$.

Optional substituents which may be present on the aromatic or heteroaromatic groups represented by the group $R^3$ include one, two, three or more substituents, each selected from an atom or group $R^{13}$ in which $R^{13}$ is —$R^{13a}$ or -Alk$^6$($R^{13a})_m$, where $R^{13a}$ is a halogen atom, or an amino (—NH$_2$), substituted amino, nitro, cyano, amidino, hydroxyl (—OH), substituted hydroxyl, formyl, carboxyl (—CO$_2$H), esterified carboxyl, thiol (—SH), substituted thiol, —COR$^{14}$ [where $R^{14}$ is an -Alk$^6$($R^{13a})_m$, aryl or heteroaryl group], —CSR$^{14}$, —SO$_3$H, —SOR$^{14}$, —SO$_2$R$^{14}$, —SO$_3$R$^{14}$, —SO$_2$NH$_2$, —SO$_2$NHR$^{14}$, —SO$_2$N(R$^{14})_2$, —CONH$_2$, —CSNH$_2$, —CONHR$^{14}$, —CSNHR$^{14}$, —CON[R$^{14}$]$_2$, —CSN(R$^{14})_2$, —N(R$^{11}$)SO$_2$R$^{14}$, —N(SO$_2$R$^{14})_2$, —NH(R$^{11}$)SO$_2$NH$_2$, —N(R$^{11}$)SO$_2$NHR$^{14}$, —N(R$^{11}$)SO$_2$N(R$^{14})_2$, —N(R$^{11}$)COR$^{14}$, —N(R$^{11}$)CONH$_2$, —N(R$^{11}$)CONHR$^{14}$, —N(R$^{11}$)CON(R$^{14})_2$, —N(R$^{11}$)CSNH$_2$, —N(R$^{11}$)CSNHR$^{14}$, —N(R$^{11}$)CSN(R$^{14})_2$, —N(R$^{11}$)CSR$^{14}$, —N(R$^{11}$)C(O)OR$^{14}$, —SO$_2$NHet$^1$ [where —NHet$^1$ is an optionally substituted C$_{5-7}$cyclicamino group optionally containing one or more other —O— or —S— atoms or —N(R$^{11}$)—, —C(O)—, —C(S)—, S(O) or —S(O)$_2$ groups], —CONHet$^1$, —CSNHet$^1$, —N(R$^{11}$)SO$_2$NHet$^1$, —N(R$^{11}$)CONHet$^1$, —N(R$^{11}$)CSNHet$^1$, —SO$_2$N(R$^{11}$)Het$^2$ [where Het$^2$ is an optionally substituted monocyclic C$_{5-7}$carbocyclic group optionally containing one or more —O— or —S— atoms or —N(R$^{11}$)—, —C(O)— or —C(S)— groups], -Het$^2$, —CON(R$^{11}$)Het$^2$, —CSN(R$^{11}$)Het$^2$, —N(R$^{11}$)CON(R$^{11}$)Het$^2$, —N(R$^{11}$)CSN(R$^{11}$)Het$^2$, aryl or heteroaryl group; Alk$^6$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N(R$^{15}$)— groups [where $R^{15}$ is a hydrogen atom or C$_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -Alk$^6$($R^{13a})_m$, m is an integer 1, 2 or 3, it is to be understood that the substituent or substituents $R^{13a}$ may be present on any suitable carbon atom in -Alk$^6$. Where more than one $R^{13a}$ substituent is present these may be the same or different and may be present on the same or different atom in -Alk$^6$. Clearly, when m is zero and no substituent $R^{13a}$ is present the alkylene, alkenylene or alkynylene chain represented by Alk$^6$ becomes an alkyl, alkenyl or alkynyl group.

When $R^{13a}$ is a substituted amino group it may be for example a group —NHR$^{14}$ [where $R^{14}$ is as defined above] or a group —N(R$^{14})_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group $R^{13a}$ include groups of formula —CO$_2$Alk$^8$ wherein Alk$^8$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^8$ group include $R^{13a}$ substituents described above.

When Alk$^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^8$)— groups.

Aryl or heteroaryl groups represented by the groups $R^{13a}$ or $R^{14}$ include mono- or bicyclic optionally substituted C$_{6-12}$aromatic or C$_{1-9}$hetero-aromatic groups as described above for the group Ar$^1$. The aromatic and heteroaromatic groups may be attached to the remainder of the compound of formula (1) by any carbon or hetero e.g. nitrogen atom as appropriate.

When —NHet$^1$ or -Het$^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or -Het$^2$ include those optional substituents described above in relation to aliphatic chains represented by Alk$^1$.

Particularly useful atoms or groups represented by $R^{13}$ include fluorine, chlorine, bromine or iodine atoms, or $C_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, $C_{1-6}$hydroxyalkyl, e.g. hydroxymethyl or hydroxyethyl, carboxy$C_{1-6}$alkyl, e.g. carboxyethyl, $C_{1-6}$alkylthio e.g. methylthio or ethylthio, carboxy$C_{1-6}$ alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, optionally substituted phenoxy, pyridyloxy, thiazolyoxy, phenylthio or pyridylthio, $C_{4-7}$cycloalkyl, e.g. cyclobutyl, cyclopentyl, $C_{5-7}$cycloalkoxy, e.g. cyclopentyloxy, halo$C_{1-6}$alkyl, e.g. trifluoromethyl, halo$C_{1-6}$alkoxy, e.g. trifluoromethoxy, $C_{1-6}$alkylamino, e.g. methylamino, ethylamino or propylamino, $C_{6-12}$aryl$C_{1-6}$alkylamino, e.g. benzylamino, 4-fluorobenzyl-amino or 4-hydroxyphenylethylamino, amino (—$NH_2$), amino$C_{1-6}$alkyl, e.g. aminomethyl or aminoethyl, $C_{1-6}$dialkylamino, e.g. dimethylamino or diethylamino, amino$C_{1-6}$alkylamino, e.g. aminoethylamino or amino-propylamino, optionally substituted $Het^1NC_{1-6}$ alkylamino, e.g. 3-morpho-linopropylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$ alkoxy, e.g. methylaminoethoxy, $C_{1-6}$dialkylamino$C_{1-6}$ alkoxy, e.g. dimethylaminoethoxy, diethylaminoethoxy, diisopropylaminoethoxy, or dimethylaminopropoxy, hydroxy$C_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—$CO_2H$), —$CO_2Alk^8$ [where $Alk^8$ is as defined above], $C_{1-6}$alkanoyl e.g. acetyl, propyryl or butyryl, optionally substituted benzoyl, thiol (—SH), thio$C_{1-6}$alkyl, e.g. thiomethyl or thioethyl, —SC(=NH)$NH_2$, sulphonyl (—$SO_3H$), —$SO_3Alk^8$, $C_{1-6}$alkylsulphinyl, e.g. methylsulphinyl, ethylsulphinyl or propylsulphinyl, $C_{1-6}$alkylsulphonyl, e.g. methylsulphonyl, ethylsulphonyl or propyl-sulphonyl, aminosulphonyl (—$SO_2NH_2$), $C_{1-6}$alkylaminosulphonyl, e.g. methylaminosulphonyl, ethylaminosulphonyl or propylaminosulphonyl $C_{1-6}$dialkylaminosulphonyl, e.g. dimethylaminosulphonyl or diethylamino-sulphonyl, phenylaminosulphonyl, carboxamido (—$CONH_2$), $C_{1-6}$alkylamino-carbonyl, e.g. methylaminocarbonyl, ethylaminocarbonyl or propylamino-carbonyl, $C_{1-6}$dialkylaminocarbonyl, e.g. dimethylaminocarbonyl or diethylaminocarbonyl, amino$C_{1-6}$ alkylaminocarbonyl, e.g. aminoethyl-aminocarbonyl, $C_{1-6}$alkylamino$C_{1-6}$alkylaminocarbonyl, e.g. methylamino-ethylaminocarbonyl, $C_{1-6}$dialkylamino$C_{1-6}$ alkylaminocarbonyl, e.g. diethyl-aminoethylaminocarbonyl, aminocarbonylamino, $C_{1-6}$alkylaminocarbonyl-amino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, —CONHC(=NH)$NH_2$, $C_{1-6}$alkylsulphonylamino, e.g. methylsulphonylamino or ethylsulphonylamino, halo$C_{1-6}$alkylsulphonylamino, e.g. trifluoromethylsulphonylamino, $C_{1-6}$dialkylsulphonylamino, e.g. dimethylsulphonylamino or diethylsulphonylamino, optionally substituted phenylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$ alkyl, e.g. acetylaminomethyl, $C_{1-6}$alkanoylamino$C_{1-6}$ alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^3$.

When the groups $R^x$ and $R^y$ are joined together to form an optionally substituted spiro linked cycloaliphatic or heterocycloaliphatic group joined to the cyclobutenone ring as defined by formula (1) it may be any such cycloaliphatic or heterocycloaliphatic group as previously described for $R^3$. Optional substituents which may be present on such spiro linked cycloaliphatic or heteroaliphatic groups include those optional substituents as described in relation to $R^3$.

The presence of certain substituents in the compounds of formulae (1), (2) or $Ar^1W$ may enable salts of the compounds to be used. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

In compounds of formulae (1) or $Ar^1W Ar^1$ is preferably an optionally substituted phenyl, monocyclic heteroaromatic or bicyclic heteroaromatic group. Particularly useful monocyclic heteroaromatic groups are optionally substituted fiveor six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these monocyclic $Ar^1$ groups include halogen atoms or alkyl, haloalkyl, —$OR^6$, —$SR^6$, —$NR^6R^7$, —$CO_2H$, —$CO_2CH_3$, —$NO_2$, —$N(R^6)COR^7$ or —CN groups as described above in relation to the compounds of formula (1). Particularly useful bicyclic heteroaromatic groups represented by $Ar^1$ include optionally substituted ten-membered fused-ring heteroaromatic groups containing one, two or three, especially one or two heteroatoms, especially nitrogen atoms. Particular examples include optionally substituted naphthyridinyl, especially 2,6-naphthyridinyl, 2,7-naphthyridinyl, quinolinyl and isoquinolinyl, especially isoquinolin-1-yl groups. Particular optional substituents include those just described for monocyclic heteroaromatic groups.

The process according to the invention is particularly useful for the preparation of compounds of formula (1b):

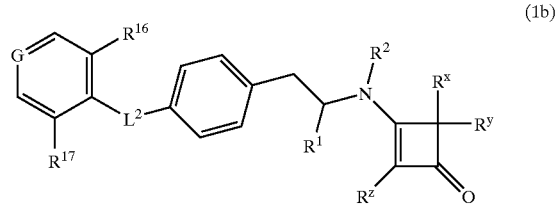

(1b)

wherein -G= is —$CR^{18}$=, —N= or —N(O)=;

$R^{16}$, $R^{17}$ and $R^{18}$, which may be the same or different is each a hydrogen atom or an atom or group -$L^3(Alk^2)_tL^4(R^5)_u$ in which $L^3$, $Alk^2$, t, $L^4$, $R^5$ and u are as defined previously;

$L^2$, $R^1$, $R^2$, $R^x$, $R^y$ and $R^z$ are as defined for formula (1); and the salts, solvates, hydrates and N-oxides thereof.

In one preferred class of compounds of formula (1b) where G is a —$CR^{18}$= group $R^{18}$ is a hydrogen atom. In another preferred class of compounds $R^{18}$ is a preferred atom or group as hereinafter defined for $R^{16}$, especially a $C_{1-6}$alkoxy, especially a methoxy or ethoxy, group.

In another preferred class of compounds of formula (1b) G is a —N= or —N(O)= group.

$R^{16}$ and $R^{17}$ in compounds of formula (1b) is each preferably as particularly described above for compounds of formula (1), other than a hydrogen atom. Particularly useful $R^{16}$ and $R^{17}$ substituents include halogen atoms, especially fluorine or chlorine atoms, or $C_{1-6}$alkyl, especially methyl, ethyl or isopropyl, halo$C_{1-6}$alkyl especially halomethyl, most especially —$CF_3$, —$CHF_2$ or —$CH_2F$, $C_{1-6}$alkoxy especially methoxy or etoxy or halo$C_{1-6}$alkoxy especially halomethoxy, most especially —$OCF_3$, —$OCHF_2$ or —$OCH_2F$ groups.

A further group of compounds particularly prepared according to the process of the invention has the formula (1c):

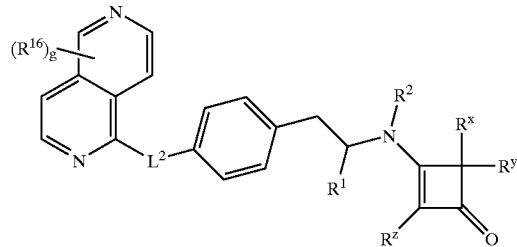

(1c)

wherein g is the integer 1, 2, 3 or 4;

$R^{16}$, is an atom or group -$L^3(Alk^2)_tL^4(R^5)_u$ in which $L^3$, $Alk^2$, t, $L^4$, $R^5$ and u are as defined previously;

$L^2$, $R^1$, $R^2$, $R^x$, $R^y$ and $R^z$ are as defined for formula (1); and the salts, solvates, hydrates and N-oxides thereof.

Particular $R^{16}$ substituents when present in compounds of formula (1c) include halogen atoms, especially fluorine, chlorine or bromine atoms, or $C_{1-6}$alkyl e.g. methyl, ethyl or isopropyl, halo$C_{1-6}$alkyl, especially halomethyl, most especially —$CF_3$, $C_{1-6}$alkoxyl, especially methoxy, halo$C_{1-6}$alkoxy, especially halomethoxy, most especially —$OCF_3$, —CN, —$CO_2CH_3$, —$NO_2$, amino (—$NH_2$), substituted amino (—$NR^6R^7$) especially —$NHCH_3$ and —$N(CH_3)_2$, —$N(R^6)COCH_3$, especially —$NHCOCH_3$ groups or optionally substituted phenyl, furyl, thienyl, imidazolyl, pyridyl and pyrimidinyl groups.

The process is also particularly useful for the preparation of compounds of formula (1d):

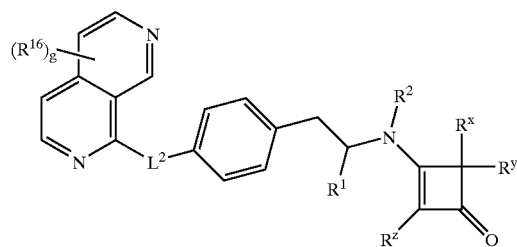

(1d)

wherein $R^{16}$, g, $L^2$, $R^1$, $R^2$, $R^x$, $R^y$ and $R^z$ are as defined for formula (1c); and the salts, solvates, hydrates and N-oxides thereof.

Each $R^{16}$ atom or group in compounds of formula (1d) may be independently selected from an atom or group -$L^3(Alk^2)_nL^4(R^5)_u$ as previously particularly defined for compounds of formula (1c).

A further particularly useful group of compounds prepared according to the process of the invention has the formula (1e):

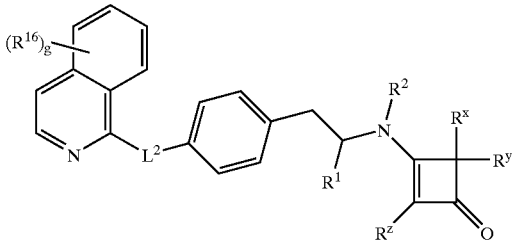

(1e)

wherein $R^{16}$, g, $L^2$, $R^1$, $R^2$, $R^x$, $R^y$ and $R^z$ are as defined for formula (1c): and the salts, solvates, hydrates and N-oxides thereof.

Each $R^{16}$ atom or group in compounds of formula (1e) may be independently selected from an atom or group -$L^3(Alk^2)_tL^4(R^5)_u$ as previously defined for compounds of formula (1c).

In one preferred class of compounds of formula (1e) at least one $R^{16}$ atom or group is present at the 3-position of the isoquinoline ring. In a preferred group of compounds of this class $R^{16}$ is an optionally substituted phenyl ring. Optional substituents which may be present on the phenyl ring include halogen atoms, especially fluorine or chlorine atoms, or $C_{1-6}$alkyl, especially methyl, ethyl or isopropyl, halo$C_{1-6}$alkyl especially halomethyl, most especially —$CF_3$, —$CHF_2$ or —$CH_2F$, $C_{1-6}$alkoxy especially methoxy or etoxy or halo$C_{1-6}$alkoxy especially halomethoxy, most especially —$OCF_3$, —$OCHF_2$ or —$OCH_2F$ groups.

It will be understood that compounds according to formulae (1b), (1c), (1d) and (1e) include, where applicable, the corresponding hydroxy tautomers.

It will be appreciated that the processes used to prepare the compounds of formulae (1b), (1c), (1d) and (1e) each comprise reacting a compound of formula $Ar^1W$, wherein $Ar^1$ is the particularly preferred aryl or heteroaryl group, with a compound of formula (2) using the methods as described herein.

In one particular aspect of the invention compounds of formulae (1), (1b), (1c), (1d) and (1e) are prepared wherein $R^1$ is a —$CO_2H$ group.

In another particular aspect of the invention compounds of formulae (1), (1b), (1c), (1d) and (1e) are prepared wherein $R^1$ is an esterified carboxyl group of formula —$CO_2Alk^7$ which may advantageously be used as a prodrug of the active compound. In this class of compound $Alk^7$ is preferably a $C_{1-8}$alkyl group, especially a methyl, ethyl, propyl, i-propyl, butyl, t-butyl, pentyl or neopenyl group; an optionally substituted $C_{3-8}$cycloalkyl group, especially a cyclopropyl, cyclobutyl, cyclopentyl, cyclohexyl or cycloheptyl group; an optionally substituted $C_{3-8}$heterocycloalkyl group especially a tetrahydrofuanyl e.g. tetrahydrofuran-3-yl, pyrrolidinyl e.g. 1-methylpyrrolidinyl such as 1-methylpyrrolidin-3-yl, piperidinyl e.g. 1-methylpiperidinyl such as 1-methylpiperidin-4-yl, tetrahydropyranyl e.g. tetrahydropyran-4-yl or 2-oxo-[1,3]dioxol-4-yl e.g. 5-methyl-2-oxo-[1,3]dioxol-4-yl group; an optionally substituted $C_{6-10}$aryl group, especially a phenyl group; an optionally substituted $C_{6-10}$aryl$C_{1-6}$alkyl group, especially a benzyl group; an optionally substituted hetero$C_{6-10}$aryl$C_{1-6}$alkyl group, especially a pyridinyl$C_{1-3}$alkyl group such as pyridinylmethyl e.g. pyridin-4-ylmethyl or pyridinylethyl e.g. pyridine-4-ylethyl or a imidazolyl$C_{1-3}$alkyl group such as imidazolylethyl e.g. 2imidazol-1-ylethyl or imidazolylpropyl e.g. 2-imidazol-1-ylpropyl group; an optionally substituted hydroxy$C_{1-6}$alkyl group, especially a hydroxyethyl e.g. 2-hydroxyethyl or hydroxypropyl e.g. 3-hydroxypropyl or 2,3-dihydroxypropyl group; an optionally substituted $C_{3-8}$heterocycloalkyl$C_{1-6}$alkyl group, especially a morpholinyl-N-ethyl group; an optionally substituted N-di-$C_{1-8}$alkylamino$C_{1-8}$alkyl group, especially a N-dimethylaminoethyl or N-diethylaminoethyl group; or an optionally substituted $C_{1-6}$alkyloxy$C_{1-6}$alkyl group, especially a methyloxyethyl group. Especially preferred esterified carboxyl groups include —$CO_2CH_3$, —$CO_2CH_2CH_3$, —$CO_2CH_2CH_2CH_3$, —$CO_2CH(CH_3)_2$ and —$CO_2C(CH_3)_3$ groups.

The process is especially useful for preparing esterified carboxyl groups (—$CO_2Alk^7$) which are selected from —$CO_2$(hydroxy$C_{1-6}$alkyl), especially —$CO_2CH_2CH_2OH$ or —$CO_2CH_2CH_3$.

In general in compounds of formula (1), (1b), (1c), (1d), (1e), (2), (4) and (5) $R^2$ is preferably a hydrogen atom.

In one preferred aspect compounds of formula (1b) are prepared wherein $L^2$ is a —$CON(R^4)$— group [where $R^4$ is preferably a hydrogen atom or a $C_{1-3}$alkyl group], especially a —CONH— group. In this class of compounds -G= is preferably —N= or —N(O)=. Most preferably G is —N=.

In another preferred aspect compounds of formulae (1c), (1d) and (1e) are prepared wherein $L^2$ is a —$N(R^4)$— group [where $R^4$ is preferably a hydrogen atom or a $C_{1-3}$alkyl group]. An especially preferred —$N(R^4)$— group is —NH—.

In one generally preferred aspect compounds of formulae (1), (1b), (1c), (1d) and (1e) are prepared wherein $R^x$, $R^y$ and/or $R^z$ is an optionally substituted alkyl group, most preferably an optionally substituted $C_{1-8}$alkyl group such as a methyl, ethyl, n-propyl, i-propyl, n-butyl, n-heptyl, or n-hexyl group. Particularly preferred optional substituents which may be present on such $R^x$, $R^y$ and/or $R^z$ alkyl groups include halogen atoms, especially fluorine or chlorine atoms, $C_{1-6}$alkoxy groups, especially methoxy, halo$C_{1-6}$alkoxy groups, especially —$OCF_3$, —CN, —$CO_2CH_3$, —$NO_2$, substituted amino (—$NR^6R^7$) especially —$NHCH_3$ and —$N(CH_3)_2$ and optionally substituted phenyl groups where the optional substituents include halogen atoms, especialy fluorine, chlorine or bromine atoms, or $C_{1-6}$alkyl e.g. methyl, ethyl or i-propyl, halo$C_{1-6}$alkyl especially halomethyl, most especialy —$CF_3$, $C_{1-6}$alkoxy especially methoxy or halo$C_{1-6}$alkoxy, especially halomethoxy, most especially —$OCF_3$, —CN, —$CO_2CH_3$, —$NO_2$, amino (—$NH_2$), substituted amino ($NR^6R^7$) especially —$NHCH_3$ and —$N(CH_3)_2$ and —$N(R^6)COCH_3$, especially —$NHCOCH_3$ groups.

In one generally preferred aspect compounds of formulae (1), (1b), (1c), (1d) and (1e) are prepared wherein $R^x$, $R^y$ and/or $R^z$ is an optionally substituted alkyl group, most preferably an optionally substituted $C_{1-8}$alkyl group such as a methyl, ethyl, n-propyl, i-propyl, n-butyl, n-heptyl, or n-hexyl group. Particularly preferred optional substituents which may be present on such $R^x$, $R^y$ and/or $R^z$ alkyl groups include halogen atoms, especially fluorine or chlorine atoms, $C_{1-6}$alkoxy groups, especially methoxy, halo$C_{1-6}$alkoxy groups, especially —$OCF_3$, —CN, —$CO_2CH_3$, —$NO_2$, substituted amino (—$NR^6R^7$) especially —$NHCH_3$ and —$N(CH_3)_2$ and optionally substituted phenyl groups where the optional substituents are as herein defined above.

In another preferred aspect compounds of formulae (1), (1b), (1c), (1d) and (1e) are prepared wherein $R^z$ is a hydrogen atom.

In another preferred aspect compounds of formulae (1), (1b), (1c), (1d) and (1e) are prepared wherein $R^x$ is a hydrogen atom.

In another preferred aspect compounds of formulae (1), (1b), (1c), (1d) and (1e) are prepared wherein $R^z$ is a halogen atom, especially a fluorine, chlorine, bromine or iodine atom, most especially a chlorine or bromine atom.

In another preferred aspect compounds of formulae (1), (1b), (1c), (1d) and (1e) are prepared wherein $R^z$ is a group -$L^1(Alk^1)_nR^3$. In this class of compounds $L^1$ is preferably a covalent bond or an —O—, —S— or —Se— atom or —S(O)— or —N($R^8$)—, especially —NH— or —N(CH$_3$)— group. Most preferably $L^1$ is a —S— atom or —S(O)— group. In this class of compounds $R^3$ is preferably a hydrogen atom or an optionally substituted $C_{3-10}$cycloaliphatic, especially $C_{3-7}$cycloalkyl group, most especially an optionally substituted cyclopentyl, cyclohexyl or cycloheptyl group; or an optionally substituted $C_{3-10}$heterocycloaliphatic, especially $C_{3-7}$heterocycloalkyl group, most especially an optionally substituted piperidinyl, piperazinyl, pyrrolidinyl, imidazolidinyl, dithianyl or pyrazolidinyl group, or an optionally substituted $C_{6-12}$aromatic group, preferably an optionally substituted phenyl group or an optionally substituted $C_{1-9}$heteroaromatic group, preferably an optionally substituted monocyclic $C_{1-9}$heteroaromatic group, most preferably a 5- or 6-membered monocyclic heteroaromatic group containing one, two, three or four heteroatoms selected from oxygen, sulphur or nitrogen atoms, especially an optionally substituted furyl, thienyl, imidazolyl e.g. 1-methylimidazol-2-yl, triazolyl, tetrazolyl, pyridyl, pyrimidinyl or pyrazinyl group. Optional substituents which may be present on such heterocycloaliphatic groups include those substituents as described hereinafter when $R^x$ and $R^y$ are joined to form an optionally substituted spiro linked heterocycloaliphatic group. Optional substituents which may be present on such aromatic and heteroaromatic groups include those substituents as described hereinbefore in relation to $R^{16}$ substituents in compounds of formula (1b). In one preferred group of compounds of this class n is zero. In another preferred group of compounds of this class $L^1$ is a covalent bond and n is zero. In this group of compounds $R^3$ is preferrably an optionally substituted $C_{3-10}$cycloaliphatic, $C_{3-10}$heterocycloaliphatic, $C_{6-12}$aromatic or monocyclic $C_{1-9}$heteroaromatic group as just described. In a further preferred group of compounds of this class n is the integer 1 and $Alk^1$ is preferably an optionally substituted aliphatic chain, most preferably an optionally substituted $C_{1-6}$alkylene chain, especially a —CH$_2$—, —CH$_2$CH$_2$— or —CH$_2$CH(CH$_3$)— chain. In a further preferred group of compounds of this class $L^1$ is a covalent bond, n is the integer 1 and $Alk^1$ is preferably an optionally substituted aliphatic chain, most preferably an optionally substituted $C_{1-6}$alkylene chain, especially a —CH$_2$—, —CH$_2$CH$_2$—, —CH$_2$CH$_2$CH$_2$— or —CH$_2$CH(CH$_3$)— chain. In a further preferred group of compounds of this class $L^1$ is a preferred atom or group as just described, most especially a —S— atom, n is the integer 1 and $Alk^1$ is preferably an optionally substituted aliphatic chain, most preferably an optionally substituted $C_{1-6}$alkylene chain, especially a —CH$_2$—, —CH$_2$CH$_2$—, —CH$_2$CH$_2$CH$_2$— or —CH$_2$CH(CH$_3$)— chain. In this class of compounds $R^3$ is preferably a hydrogen atom.

Most especially preferred $R^z$ groups which may be prepared using the process of the invention include a hydrogen or halogen atom, especially fluorine, chlorine, bromine or iodine atom or a group of formula -$L^1(Alk^1)_nR^3$ as just defined, especially an alkyl group as previously described or a hydroxyl (—OH); $C_{1-6}$alkoxymethoxy, ethoxy or i-propoxy; $C_{3-7}$cycloalkyl, especially cyclopentyl or cyclohexyl; $C_{1-6}$alkylsulfanyl, especially methyl- ethyl- or i-propylsulfanyl; $C_{1-6}$alkylsulfinyl, especially methyl- ethyl- or i-propylsulfinyl; $C_{3-7}$heterocycloalkyl, especially piperidinyl most especially piperidin-3-yl such as 1-methylpiperidin-3-yl or dithianyl especially [1,3]dithian-2-yl; $C_{6-12}$arylselenenyl, especially phenylselenenyl; $C_{6-12}$arylsulfanyl, especially phenylsulfanyl or pentafluorophenylsulfanyl; monocyclic $C_{1-9}$heteroaromaticsulfanyl, especially tetrazol-5-ylsulfanyl most especially 1-methyl-1H-terazol-5-ylsulfanyl or imidazolylsulfanyl especially imidazol-2-ylsulfanyl most especially 1-methyl-1H-imidazol-2-ylsulfanyl; monocyclic $C_{1-9}$heteroaromatic, especially pyridinyl most especially pyridin-3-yl, 1-methylpyridinium or pyrazinyl especially pyrazin-2-yl; or a $C_{6-12}$aryl$C_{1-3}$alkyl, especially benzyl group.

In another preferred aspect compounds of formulae (1), (1b), (1c), (1d) and (1e) are prepared wherein $R^x$ and $R^z$ is each a hydrogen atom.

In another preferred aspect compounds of formulae (1), (1b), (1c), (1d) and (1e) are prepared wherein $R^x$ is a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred aspect compounds of formulae (1), (1b), (1c), (1d) and (1e) are prepared wherein $R^x$ and $R^y$ is each a hydrogen atom and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred aspect compounds of formulae (1), (1b), (1c), (1d) and (1e) are prepared wherein $R^x$ is a hydrogen atom and $R^y$ is an optionally substituted alkyl group as just described for generally preferred alkyl groups.

In another preferred aspect compounds of formulae (1), (1b), (1c), (1d) and (1e) are prepared wherein $R^x$ and $R^z$ is each a hydrogen atom and $R^y$ is an optionally substituted alkyl group as just described.

In another preferred aspect compounds of formulae (1), (1b), (1c), (1d) and (1e) are prepared wherein $R^x$ is a hydrogen atom, $R^z$ is a halogen atom, especially a fluorine, chlorine, bromine or iodine atom, most especially a chlorine or bromine atom or $R^z$ is a group -$L^1(Alk^1)_nR^3$, especially a group as just particularly described, and $R^y$ is an optionally substituted alkyl group as just described for generally preferred alkyl groups.

In another preferred aspect compounds of formulae (1), (1b), (1c), (1d) and (1e) are prepared wherein $R^x$ is a hydrogen atom and $R^y$ and $R^z$ is each an optionally substituted alkyl group as just described for generally preferred alkyl groups.

In another preferred aspect compounds of formulae (1), (1b), (1c), (1d) and (1e) are prepared wherein $R^x$ and $R^y$ is each an optionally substituted alkyl group as just described for generally preferred alkyl groups.

In another preferred aspect compounds of formulae (1), (1b), (1c), (1d) and (1e) are prepared wherein $R^x$ and $R^y$ is each an optionally substituted alkyl group as just described for generally preferred alkyl groups and $R^z$ is a hydrogen atom.

In another preferred aspect compounds of formulae (1), (1b), (1c), (1d) and (1e) are prepared wherein $R^x$ and $R^y$ is each an optionally substituted alkyl group as just described for generally preferred alkyl groups and $R^z$ is a halogen atom, especially a fluorine, chlorine, bromine or iodine atom, most especially a chlorine or bromine atom, or $R^z$ is a group -$L^1(Alk^1)_nR^3$ as just described.

In another preferred aspect compounds of formulae (1), (1b), (1c), (1d) and (1e) are prepared wherein $R^x$, $R^y$ and $R^z$ is each an optionally substituted alkyl group as just described for generally preferred alkyl groups.

In another preferred aspect compounds of formulae (1), (1b), (1c), (1d) and (1e) are prepared wherein $R^x$ and $R^y$ are joined to form an optionally substituted spiro linked cycloaliphatic group particularly a $C_{3-10}$cycloaliphatic group, most particularly a $C_{3-8}$cycloalkyl group, especially an optionally substituted cyclopentyl cyclohexyl, cycloheptyl or cyclooctyl group, or a $C_{3-8}$cycloalkenyl group, especially an optionally substituted cyclopentenyl, cyclohexenyl, cycloheptenyl or cyclooctenyl group group. Particularly preferred optional substituents which may be present on such spiro linked cycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —OCF$_3$, —CN, —CO$_2$CH$_3$, —NO$_2$ and substituted amino (—N($R^{11}$)$_2$), especially —NHCH$_3$ and —N(CH$_3$)$_2$ groups. In a preferred group of compounds of this class $R^z$ is a hydrogen atom. In another preferred group of compounds of this class $R^z$ is an alkyl group as just described. In a further preferred group of compounds of this class $R^z$ is a halogen atom, especially a fluorine, chlorine, bromine or iodine atom, most especially a chlorine or bromine atom, particularly a bromine atom. In a still further preferred group of compounds of this class $R^z$ is a group -$L^1$(Alk$^1$)$_n$$R^3$ as just described.

In another preferred aspect compounds of formulae (1), (1b), (1c), (1d) and (1e) are prepared wherein $R^x$ and $R^y$ are joined to form an optionally substituted spiro linked heterocycloaliphatic group, particularly an optionally substituted $C_{3-10}$heterocycloaliphatic group, most particularly an optionally substituted $C_{3-7}$heterocycloalkyl group, especially an optionally substituted $C_{3-7}$heterocycloalkyl group containing one or two —O—, —S—, —S(O)—, —S(O)$_2$—, —NH— or —C(O)— heteroatoms or heteroatom-containing groups. Especially preferred optionally substituted heterocycloaliphatic groups include optionally substituted 5- and 6-membered heterocycloalkyl groups containing one heteroatom or heteroatom-containing group as just described, especially optionally substituted pyrrolidinyl, tetrahydrofuranyl, tetrahydrothiophenyl, tetrahydrothiophene-1-oxide, tetrahydrothiophene-1,1-dioxide, piperidinyl, tetrahydropyranyl, tetrahydrothiopyranyl tetra-hydrothiopyran-1-oxide or tetrahydrothiopyran-1,1-dioxide groups. Particularly preferred optional substituents which may be present on such spiro linked heterocycloaliphatic groups include halogen atoms, especially fluorine or chlorine atoms, $C_{1-6}$alkyl groups, especially methyl, ethyl, propyl or i-propyl, $C_{1-6}$alkoxy groups, especially methoxy or ethoxy, halo$C_{1-6}$alkoxy groups, especially —OCF$_3$, —CN, —CO$_2$CH$_3$, —NO$_2$ and substituted amino (—N($R^{11}$)$_2$), especially —NHCH$_3$ and —N(CH$_3$)$_2$ groups. In addition when the spiro linked heterocycloaliphatic group contains a nitrogen atom this may be substituted by a group -(L$^6$)$_p$(Alk$^5$)$_q$$R^{12}$ where L$^6$ is preferably —C(O)— or —S(O)$_2$—, Alk$^5$ is preferably an optionally substituted $C_{1-6}$alkylene chain, especially a —CH$_2$—, —(CH$_2$)$_2$— or —CH(CH$_3$)CH$_2$— chain or an optionally substituted heteroC$_{1-6}$alkylene chain, especially —CH$_2$L$^5$—, —CH$_2$CH$_2$L$^5$—, -L$^5$CH$_2$— or -L$^5$CH$_2$CH$_2$ chain where L$^5$ is an —O— or —S— atom or —NH or —N(CH$_3$)— group and $R^{12}$ is a hydrogen atom or an optionally substituted phenyl ring where preferred optional substituents include those atoms and groups as defined hereinbefore for $R^{16}$ in relation to formula (2b). In one preferred group of compounds of this class $R^z$ is a hydrogen atom. In another preferred group of compounds of this class $R^z$ is an alkyl group as just described. In a further preferred group of compounds of this class $R^z$ is a halogen atom, especially a fluorine, chlorine, bromine or iodine atom, most especially a chlorine or bromine atom. In a still further preferred group of compounds of this class $R^z$ is a group -$L^1$(Alk$^1$)$_n$$R^3$ as just described.

The process is particularly suitable for the preparation of the following compounds:

(2S)-2-[(2-bromo-3-oxospiro[3.5]non-1-en-1-yl)amino]-3-{4-[(3,5-dichloroisonicotinoyl)amino]phenyl}propanoic acid;

(2S)-2-(2-bromo-3-oxo-spiro[3.5]non-1-en-1-ylamino)-3-[4-([2,7]naphthyridin-1-ylamino)phenyl]propionic acid;

(2S)-2-[(2-isopropylsulfanyl-3-oxo-7-oxa-spiro[3.5]non-1-en-1-yl)amino]-3-[4-([2,7]naphthyridin-1-ylamino) phenyl]propanoic acid and the salts, solvates, hydrates and N-oxides thereof.

The process is most especially suitable for the preparation of the following compounds:

ethyl (2S)-2-[(2-bromo-3-oxospiro[3.5]non-1-en-1-yl) amino]-3-{4-[(3,5-dichloroisonicotinoyl)amino] phenyl}propanoate;

ethyl (2S)-2-(2-bromo-3-oxo-spiro[3.5]non-1-en-1-ylamino)-3-[4-([2,7]naphthyridin-1-ylamino)phenyl] propanoate;

ethyl (2S)-2-[(2-isopropylsulfanyl-3-oxo-7-oxa-spiro[3.5] non-1-en-1yl)amino]-3-[4-([2,7]naphthyridin-1-ylamino) phenyl]propanoate;

and the salts, solvates, hydrates and N-oxides thereof.

The process is also most especially suitable for the preparation of:

2-hydroxyethyl (2S)-2-(2-bromo-3-oxo-spiro[3.5]non-1-en-1-ylamino)-3-{4-[(3,5-dichloroisonicotinoyl)amino] phenyl}propanoate;

and the salts, solvates, hydrates and N-oxides thereof.

Compounds of formulae (1), (1b), (1c), (1d) and (1e) are potent and selective inhibitors of α4 integrins. The compounds are of use in modulating cell adhesion and in particular are of use in the prophylaxis and treatment of diseases or disorders including inflammation in which the extravasation of leukocytes plays a role. Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease. The use and formulation of the compounds is more particularly described in our co-pending International Patent Application PCT/GB 02/00206.

For convenience the description hereinafter refers to the preparation of a compound of formula (1) but clearly the description applies equally to the preparation of compounds of formulae (1b), (1c), (1d) and (1e).

Thus in the process of the invention a substituted 4-aminophenylalanine of formula (2) is reacted with a compound Ar$^1$W to give a compound of formula (1). Suitable conditions for this reaction depend upon the nature of the group W.

Thus when W is the group $X^1$ the reaction may be carried out in the presence of an acid, such as a Bronsted acid e.g. hydrogen chloride. The acid may be generated in situ as a reaction by-product or may be added at the start of the reaction as an initiator e.g. catalytic amount of hydrogen chloride. The reaction may be performed in a variety of solvents such as alcohols e.g. ethanol, ethers e.g. tetrahydrofuran, 2-methoxyethyl ether, 1,4-dioxane, acetic acid, water, acetonitrile, substituted amides such as N,N-dimethylformamide or acetates e.g. ethyl acetate.

In one particular aspect of the process $X^1$ is a halogen atom, especially a chlorine or bromine atom.

Compounds of formula $Ar^1X^1$ may be prepared from alcohols of formula $Ar^1OH$ using methods known to those skilled in the art e.g. by reaction with a halogenating agent, for example a phosphorous oxyhalide such as phosphorous oxychloride at an elevated temperature e.g. 110° C. or by reaction with hydrogen halide e.g. hydrogen bromide.

Intermediates of formulae $Ar^1OH$ or $Ar^1X^1$ may be prepared using methods as described in co-pending International Patent Application Number WO 02/069393.

When in the process of the invention W is the group $—COX^2$ and $X^2$ is a halogen atom such as a chlorine atom the reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or a dipolar aprotic solvent such as an amide, e.g. dimethylformamide or an ether, e.g. a cyclic ether such as tetrahydrofuran or an ester e.g. ethyl acetate at for example ambient temperature. The acid chlorides $Ar^1COCl$ may be prepared from the corresponding acid using methods known to those skilled in the art.

Alternatively, the acylation may be carried out under the same conditions with an acid (i.e. where $X^2$ is —OH) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1hydroxybenzotriazole. Alternatively the acid may be reacted with a chloroformate, for example ethylchloroformate, prior to the desired acylation reaction.

It will be appreciated by those skilled in the art that acid groups may also be activated by the formation of a reactive ester e.g. ethyl or p-nitrophenyl ester.

Alternatively when in the process of the invention W is the group $—SO_2X^3$ the reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide or an ether, e.g. a cyclic ether such as tetrahydrofuran, at for example ambient temperature.

Intermediate compounds of formula (2) are novel and form a further aspect of the invention.

One particularly useful compound of formula (2) for use in the process is:
3-(4-aminophenyl)-2(S)-(3-oxo-7-oxaspiro[3.5]non-1-en-1-ylamino)-propionic acid hydroxyethyl ester.

In a further aspect of the invention intermediates of formula (2) may be prepared by reduction of a compound of formula (4):

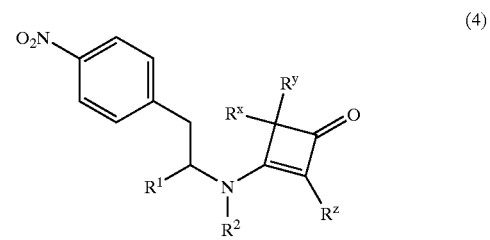

wherein $R^1$, $R^2$, $R^x$, $R^y$ and $R^z$ are as herein defined.

Suitable conditions may involve catalytic hydrogenation using for example hydrogen in the presence of a metal catalyst, for example palladium on a support such as carbon in a solvent such as an ether, e.g. tetrahydrofuran or an alcohol e.g. methanol or ethanol or an ester e.g. ethyl acetate. The reaction may be performed at atmospheric pressure or up to a pressure of 10 Bar. Alternatively chemical reduction using for example a metal, e.g. tin or iron, in the presence of an acid such as hydrochloric acid may be employed. The amine thus formed may be alkylated using conditions known to those skilled in the art to give a compound of formula (2) wherein $R^4$ is an optionally substituted straight or branched $C_{1-6}$ alkyl group.

Intermediate compounds of formula (4) are novel and form a further aspect of the invention.

One particularly useful compound of formula (4) for use in the process is: 3-(4-nitrophenyl)-2(S)-(3-oxo-7-oxaspiro[3.5]non-1-en-1-ylamino)propionic acid hydroxyethyl ester.

Thus according to a further aspect of the invention intermediates of formula (4) may be prepared by reaction of a compound of formula (5):

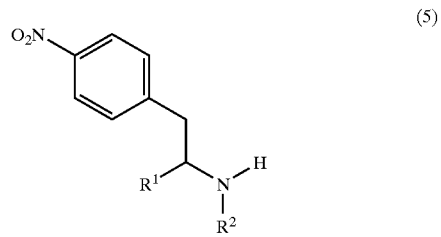

wherein $R^1$ and $R^2$ are as herein defined;
with a compound of formula (6a) or (6b):

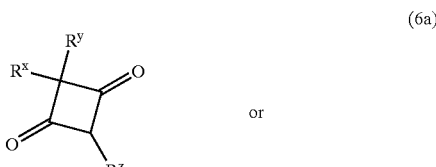

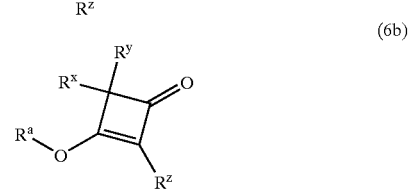

wherein Rx, Ry and Rz are as herein defined and $R^a$ represents a $C_{1-6}$ alkyl group or a silyl group. Particular silyl groups include alkylsilyl groups such as a ʹbutyldimethylsilyl or trimethylsilyl group.

The reaction may be performed in an inert solvent or mixture of solvents, for example a hydrocarbon such as an aromatic hydrocarbon e.g. benzene or toluene, a halogenated hydrocarbon such as 1,2-dichloroethane, or dichloromethane, or an ester e.g. ethyl acetate at a temperature from 0° C. to the reflux temperature. Where necessary, for example when a salt of an amine of formula (5) is used, an organic base such as diisopropylethylamine or triethylamine may be added.

Intermediates of formulae (6a) or (6b) may be prepared using methods as described in International Patent Application Number WO 02/069393.

It will be appreciated that intermediates of formula (5) where not commercially available may be prepared using methods known to those skilled in the art. For example intermediates of formula (5) in which $R^1$ is a —$CO_2Alk^7$ group may be prepared by esterification of the corresponding amino acid.

In one aspect of the process $R^1$ is especially the group —$CO_2Alk^7$.

In another aspect of the process $R^4$ is especially a hydrogen atom.

It will be appreciated that intermediates, such as intermediate $Ar^1W$, (5), (6a) or (6b), if not available commercially, may also be prepared by methods known to those skilled in the art following procedures set forth in references such as Rodd's Chemistry of Carbon Compounds, Volumes 1–15 and Supplementals (Elsevier Science Publishers, 1989), Fieser and Fieser's Reagents for Organic Synthesis, Volumes 1–19 (John Wiley and Sons, 1999), Comprehensive Heterocyclic Chemistry, Ed. Katritzky et al, Volumes 1–8, 1984 and Volumes 1–11, 1994 (Pergamon), Comprehensive Organic Functional Group Transformations, Ed. Katritzky et al, Volumes 1–7, 1995 Pergamon), Comprehensive Organic Synthesis, Ed. Trost and Flemming, Volumes 1–9, (Pergamon, 1991), Encyclopedia of Reagents for Organic Synthesis Ed. Paquette, Volumes 1–8 (John Wiley and Sons, 1995), Larock's Comprehensive Organic Transformations (VCH Publishers Inc., 1989) and March's Advanced Organic Chemistry (John Wiley and Sons, 1992).

Where desired the process according to the invention may be extended by optionally employing one or more subsequent reactions to convert a compound of formula (1) to a further compound of formula (1) as described hereinafter.

Further, compounds of formula (1) in which $R^z$ is a halogen atom may be obtained from compounds of formula (1) in which $R^z$ is a hydrogen atom by reaction with a halogen source such as bromine or a halosuccinamide e.g. chloro or bromosuccinamide. The reaction may be performed in a solvent such as an ether e.g. a cyclic ether such as tetrahydrofuran or an ester e.g. ethyl acetate at a temperature from about 0° to 30°. When bromine is used as halogen source the reaction may optionally be performed in the presence of added base such as an amine e.g. triethylamine in the presence of a halogenated hydrocarbon e.g. dichloromethane.

Further, compounds of formula (1) in which $R^z$ is a group -$L^1(Alk^1)_n(R^3)_v$ in which $L^1$ is for example a Se, S, O or $N(R^8)$ may be prepared by reaction of an intermediate of formula $HL^1(Alk^1)_n(R^3)_v$ with a compound of formula (1) in which $R^z$ is a hydrogen atom. The reaction may be performed in an organic solvent such as an ether e.g. a cyclic ether such as tetrahydrofuran at around room temperature optionally in the presence of a base such as an amine e.g. triethylamine. When $R^z$ is the group —$S(Alk^1)_n$ the reaction may be achieved using a compound of formula -$HalS(Alk^1)_n$ where Hal is a halogen atom, for example, chlorine.

It will be appreciated by one skilled in the art that the group $R^z$ may also be derivatised, for example as described above, in intermediates preceding the compounds of formula (1).

Further the compounds of formula (1) which contain the group $Alk^7$ may be interconverted to give acids or further derivatives (e.g. esters) or biosteres of formula (1).

Thus the process may be used to obtain a compound of formula (1) in which $R^1$ is a —$CO_2H$ group by hydrolysis of an ester of formula (1) wherein $R^1$ is the group —$CO_2Alk^7$. The hydrolysis may be performed using either an acid or a base depending on the nature of $Alk^7$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used. The acids thus formed may then be further derivatised, for example by esterification, using standard methods known to those skilled in the art, such as reaction with an alcohol of formula —$HOAlk^7$ in the presence of an acid catalyst e.g. p-toluenesulfonic acid. Alternatively a condensing agent, for example a diimide such as 1-(3-dimethylaminopropyl)3-ethylcarbodiimide or N,N'-dicyclohexylcarbodiimide, may be employed, advantageously in the presence of a catalyst such as a N-hydroxy compound e.g. a N-hydroxytriazole such as 1-hydroxybenzotriazole. Alternatively an ester of formula (1) may undergo transesterification, preferably in the presence of an acid catalyst, to give another ester of formula (1).

In the above processes, compounds containing a basic centre may be isolated and/or crystallised by the formation of a salt, which may offer an improvement in purity. Suitable salts include, but are not limited to oxalate or di-p-toluoyl-D-tartrate.

It will be appreciated that the compounds of formula (1), such as those as formed in the process as defined herein, or any preceding intermediates may be further derivatised by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of any of formula (1) or any preceding intermediates where appropriate functional groups exist in these compounds.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes of the invention described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following examples illustrate the present invention in more detail; however, they are not intended to limit its scope in any manner. All temperatures are in ° C. The following abbreviations are used:

EtOAc—ethyl acetate;
MeOH—methanol;
EtOH—ethanol;
DMSO—dimethylsulphoxide;
THF—tetrahydrofuran,
nBuLi—n-butyl lithium
DCM—dichloromethane;
HOAc—acetic acid;
Et$_2$O—diethyl ether;
DMF—N,N-dimethylformamide;
HOBT—1-hydroxybenzotriazole
LDA—lithium diisopropylamide
EDC—1-(3-dimethylaminopropyl)-3-ethylcarbodiimide hydrochloride All NMR's were obtained either at 300 MHz or 400 MHz.

All Intermediates and Examples were named with the aid of Beilstein Autonom (available from MDL Information Systems GmbH, Therdor-Heuss-Allee 108D 60486, Frankfurt, Germany) or were given names that seemed consistent, with the exception that propanoates were named by the IUPAC name rather than the trivial name (propionate) and isonicotinoyl (trivial name) is used in place of pyridine-4-carbonyl.

INTERMEDIATE 1

3,5-Dichloropyridine-4-carboxylic acid

A solution of 3,5-dichloropyridine (5.00 g, 33.8 mmol) in THF (25 ml) was added to a solution of LDA [generated from nBuLi (2.5 M solution in hexanes, 14.9 ml, 37.2 mmol) and diisopropylamine (4.10 g, 5.7 ml, 40.6 mmol)] in THF (25 ml) at −78° under nitrogen, to give a yellow/brown slurry. The reaction was stirred for 30 min at −78° then CO$_2$ gas was bubbled through to give a clear brown solution that slowly gave a precipitate, warmed to RT over 2 h, then quenched with water (20 ml) and partitioned between Et$_2$O (100 ml) and 1M NaOH (100 ml). The aqueous layer was separated and acidified to pH 1 with concentrated hydrochloric acid and then extracted with 10% MeOH in DCM (100 ml×3). The combined organic layers were dried (MgSO$_4$) and the solvent removed under vacuum to give a brown solid that was recrystallised from ethanol and dried under vacuum to give the title compound as pinkish crystals (2.63 g, 41%). δH (DMSO-d$^6$) 8.74 (2H, s). δC (DMSO-d$^6$) 163.5, 147.7, 141.0, 126.7.

INTERMEDIATE 2

3,5-Dichloroisonicotinoyl chloride

Intermediate 1 (150 g) was suspended in toluene (450 mL) containing dimethyl formamide (1.5 mL). As this mixture was boiled under reflux, thionyl chloride (132.8 g) was charged to it over 1 h. The reaction was complete after a further 2.0 h at 110° C. The solvent was removed at atmospheric pressure and then the residue was vacuum distilled, giving the title compound fraction as a water white oil that partially crystallised on standing (151.3 g, 92.0% yield, b.p 70–72° C./1.0 mmHg). δH (CDCl$_3$): 8.64 (2H, s). ESI$^+$ (m/z+1) 209.9

INTERMEDIATE 3

3-Cyano-4-(2-(N,N-dimethylamino)ethylen-1-yl)pyridine

A solution of 4-methyl-3-cyanopyridine [prepared according to Ref: J. Prakt. Chem. 338, 663 (1996)], (8.0 g, 67.8 mmol) and N,N-dimethylformamide diethyl acetal (11.0 g, 74.8 mmol) in dry DMF (50 ml) was stirred at 140° under N$_2$ for 2 days. An additional portion of N,N,-dimethylformamide diethyl acetal (5 g) was added and stirred at 140° for 4 h. The volatiles were removed in vacuo and the obtained dark oil partitioned between EtOAc (300 ml) and water (50 ml). The phases were separated and the aqueous layer re-extracted with EtOAc (3×100 ml). The combined organic extracts were washed with brine (30 ml), dried (Na$_2$SO$_4$), treated with activated charcoal, filtered and evaporated in vacuo to afford essentially pure title compound as a dull orange solid (10.1 g, 85%). δH (CDCl$_3$) 8.49 (1H, s), 8.25 (1h, d, J 5.9 Hz), 7.29 (1H, d, J 13.2 Hz), 7.09 (1H, d, J 5.9 Hz), 5.25 (1H, d, J 13.2 Hz) and 2.99 (6H, s); m/z (ES$^+$, 70V) 174 (MH$^+$).

INTERMEDIATE 4

1-Hydroxy-2,7-naphthyridine hydrochloride salt

HCl gas was bubbled through a stirred solution of Intermediate 3 (6.2 g, 3.58 mmol) in glacial acetic acid (50 ml) and water (0.64 ml, 3.55 mmol) for 1–2 min. The reaction mixture was stirred in a stoppered flask at 40° for 18 h. The volatiles were removed in vacuo affording a dark residue, which was treated with water (3×20 ml) and re-evaporated in vacuo. The obtained dark semi-solid was treated with 40 ml warm ethanol, ice-cooled, and the undissolved solid collected by filtration affording the title compound as a green coloured solid (5.2 g, 80%) δH (DMSO-d$^6$) 12.5 (1H, br s), 9.38 (1H, s), 8.84 (1H, d, J 7.0 Hz), 8.15 (1H, d, J 7.0 Hz), 7.89 (1H, br dd, J 7.0, 5.0 Hz) and 6.85 (1H, d, J 7.0 Hz); m/z (ES$^+$, 70V), 147 (MH$^+$).

INTERMEDIATE 5

1-Chloro-2,7-naphthyridine

Intermediate 4 (5.2 g, 28.5 mmol) was stirred with phosphorous oxychloride (75 ml) at 110° for 24 h. The volatiles were removed in vacuo affording a dark oil which was poured into an ice-bath cooled mixture of saturated aqueous NaHCO$_3$ (100 ml containing 20 g solid NaHCO$_3$) and EtOAc (100 ml). After thorough mixing the phases were separated and the aqueous layer re-extracted with EtOAc (2×75 ml). The combined organic extracts were washed with brine (15 ml), dried (Na$_2$SO$_4$) and evaporated in vacuo to afford the title compound as a yellow solid (4.0 g, 85%) δH (CDCl$_3$) 9.45 (1H, s), 8.81 (1H, d, J 5.7 Hz), 8.47 (1H, d, J 5.7 Hz), 7.66 (1H, d, J 5.7 Hz) and 7.60 (1H, d, J 5.7 Hz); m/z (ES$^+$, 70V) 165 and 167 (MH$^+$).

INTERMEDIATE 6

3-Ethoxy-7-oxaspiro[3.5]non-2-en-1-one

Tetrahydropyranyl-4-carboxylic acid (14.7 g, 0.11 mol) and DMF (0.5 ml) in DCM (150 ml) was treated dropwise with oxalyl chloride (1.1 eq, 10.9 ml, 0.12 mol). After 1 h the reaction mixture was concentrated in vacuo and the residual slurry was diluted with Et$_2$O (200 ml) and the resulting precipitate removed by filtration. The filtrate was treated with ethoxyacetylene (40% w/w solution in hexanes, 1.3 eq, 18 ml) followed dropwise with triethylamine (25 ml, 0.19 mol) and the reaction stirred for 11 d. Filtration and concentration of the filtrate in vacuo followed by chromatography (SiO$_2$, 5:1 EtOAc:hexanes) gave the title compound as a pale yellow oil (12.1 g, 59%). δH (CDCl$_3$, 300K) 4.85 (1H, s), 4.23 (2H, q, J 7.1 Hz), 3.89–3.75 (4H, m), 1.88–1.79 (4H, m), 1.47 (3H, t, J 7.1 Hz); m/z (ES$^+$, 70V) 182.9 (MH$^+$).

INTERMEDIATE 7

7-Oxaspiro[3.5]nonane-1,3-dione

Intermediate 6 (12.1 g, 0.67 mol) and 2M hydrochloric acid (26 ml) were stirred vigorously for 24 h at room temperature. The resulting solution was concentrated to dryness and the residual slurry was washed with Et$_2$O (25 ml) to give the title compound as an off-white powder (8.93 g, 0.062 mol). δH (DMSO d$^6$, 300K) 4.80 (2H, s), 3.78 (4H, t, J 5.5 Hz), 2.62 (4H t J 5.5 Hz); m/z (ES$^+$, 70V) 154.9 (MH$^+$).

INTERMEDIATE 8

3-(4-Nitrophenyl)-2(S)-(3-oxospiro[3.5]non-1-en-1-ylamino)propionic acid thyl ester Method A To a stirred solution of 4-nitro-(L)-phenylalanine ethyl ester hydrochloride salt (23.0 g) (CAS No. 58816-66-3) in dichloromethane (230 mL) and water (230 mL), was added slowly 46–48% sodium hydroxide solution (7.7 g, 1.1 mol eqs). The layers were separated and the aqueous phase extracted with dichloromethane (100 mL). The combined dichloromethane layers were washed with water (100 mL) and saturated brine (100 mL). The organic phase was dried (MgSO$_4$) prior to evaporation in vacuo to give 4-nitro-(L)-phenylalanine ethyl ester in quantitative yield. The free nitro-ester was dissolved in fresh dichloromethane (120 mL) and spiro[3,5]nonane-1,3-dione (CAS No 455264-97-8) (12.9 g) [see Wasserman, H. H. et al, J. Org. Chem., 38, 1451–1455 (1973)] was added portion-wise with stirring. Conversion to product was complete after 16 h (HPLC). The reaction mixture was diluted with dichloromethane (120 mL), washed with 11% sodium bicarbonate solution (100 mL), saturated brine (100 mL) and then dried (MgSO$_4$). The title compound was isolated in quantitative yield after removal of solvent in vacuo (32.4 g, viscous oil that crystallised slowly; m.p. 120° C.). δH (DMSO d$^6$) 8.39 (1H, d), 8.17 (2h, d), 7.56 (2H, d), 4.33 (1H, s), 4.31 (1H, m), 4.14 (2H, q), 3.29 (1H, dd), 3.15 (1H, dd), 1.43–1.70 (8H, m), 1.30 (1H, m), 1.15 (3H, t+1H, m). ESI$^+$ (m/z+1) 373.3

Method B 4-nitro-(L)-phenylalanine ethyl ester hydrochloride salt (100 g) was suspended in ethyl acetate (590 mL) and washed with 16.5% potassium carbonate solution (150 mL) at 25–30° C., followed by saturated brine (70 mL). The organic layer was then charged over 10 minutes to a slurry of spiro[3,5]nonane-1,3-dione (61.0 g) in ethyl acetate (310 mL), and the whole stirred out at 20–25° C. for 16 h. Following a satisfactory HPLC completion check, the reaction mixture was washed sequentially with 5% potassium carbonate solution (70 mL) and deionised water (70 mL). Wet ethyl acetate (672 g) was distilled out at atmospheric pressure from the organic phase; this operation also served to dry the residue. The concentrate was cooled to 30° C. prior to slow addition of heptane (88 mL), which caused the mixture became turbid. After seeding with authentic product, the preparation was left to crystallise. Once this process was underway, the mixture was cooled further to 0–5° C. and diluted with more heptane (190 mL). The title compound was filtered off, washed with cold 30% ethyl acetate in heptane (2×270 mL), and then dried in vacuo at 50° C. to give off-white crystals (m.p. 121.5–123.5° C., 131.2 g, 96.7% yield). $^1$H NMR (D$_6$-DMSO): 1.12 (1H, m); 1.18 (3H, t); 1.32 (1H, m); 1.57 (8H, m); 3.13 (1H, dd); 3.31 (1H,dd); 4.14 (2H, q); 4.33 (1H, m); 4.35(1H, s); 7.54 (2H, d); 8.17 (2H, d); 8.4 (1H, d) ppm.

INTERMEDIATE 9

3-(4-Aminophenyl)-2(S)-(3-oxospiro[3.5]non-1-en-1-ylamino)propionic acid ethyl ester Method A A solution of Intermediate 8 (30 g) in absolute ethanol (300 mL) was hydrogenated at 10 Bar, in the presence of 10% palladium on charcoal (1.5 g), at 20–25° C. The reaction was exothermic and required cooling. After circa 15 min hydrogen uptake ceased and the reaction was checked for completion by HPLC. The reaction mixture was filtered through celite, the pad washed clean with absolute ethanol (100 mL), and the title compound obtained after evaporation of the solvent as a thick oil (29.55 g, quantitative yield).

Method B

A solution of Intermediate 8 (30 g) in absolute ethanol (300 mL) was hydrogenated at 5 Bar, in the presence of (61% wet) 5% palladium on charcoal (1.5 g), at 20–30° C. The reaction was exothermic and required cooling. After circa 35 min hydrogen uptake ceased and the reaction was checked for completion by HPLC. The reaction mixture was filtered through celite, the pad washed clean with absolute ethanol (100 mL), and the title compound obtained after evaporation of the solvent as a thick oil (29.55 g, quantitative yield).

δH (DMSO d$^6$) 8.32 (1H, d), 6.88 (2H, d), 6.48 (2H, d), 4.93 (2H, b,s), 4.30 (1H, s), 4.10 (2H, q), 4.02 (1H, m), 2.88 (2H, m), 1.4–1.75 (10H, b,m), 1.16 (3H, t). ESI$^+$ (m/z+1) 343.3

INTERMEDIATE 10

3-(4-Nitrophenyl)-2(S)-(3-oxo-7-oxaspiro[3.5]non-1-en-1ylamino)propionic acid ethyl ester 4-Nitro-(L)-phenylalanine ethyl ester hydrochloride (28.6 g) was suspended in dichloromethane (290 mL) to which a solution of potassium carbonate (8.0 g) in water (100 mL) was added slowly with stirring. After removal of the aqueous phase, the organic layer was washed with water (2×50 mL) and then dried ($Na_2SO_4$). Following removal of the drying agent, solid Intermediate 7 (16.1 g) was added portion-wise to the stirred dichloromethane solution. The resulting mixture was left to stir-out overnight at 20–25° C. under nitrogen. The solution was sequentially washed with 5% aqueous sodium bicarbonate (100 mL), and water (2×50 mL), then dried ($Na_2SO_4$) prior to solvent removal in vacuo which afforded the title compound as an off-white foam (38.6 g, 99.2% yield).

δH (DMSO $d^6$) 8.78 (1H, d), 8.28 (2H, d), 7.66 (2H, d), 4.54 (1H, s), 4.52 (1H, m), 4.28 (2H, q), 3.84 (2H, dd), 3.72 (2H, q), 3.46 (1H, dd), 3.25 (1H, dd), 1.97 (2H, m), 1.38 (1H, d), 1.31 (1H, d), 1.28 (3H, t). $ESI^+$ (m/z+1) 375.2.

INTERMEDIATE 11

3-(4-Aminophenyl)-2(S)-(3-oxo-7-oxaspiro[3.5]non-1-en-1-ylamino)propionic acid ethyl ester A solution of Intermediate 10 (41.4 g) in ethanol (400 mL) was hydrogenated at 10 Bar in the presence of 5% palladium on charcoal (3.0 g) for 1 hour at 20–40° C. The catalyst was removed by filtration through celite at 40° C., under an inert atmosphere, and the cake washed with fresh ethanol (2×50 mL). After removal of circa 300 ml of alcohol by vacuum distillation of the combined liquors at 40° C., the residual solution was allowed to cool whereupon the title compound crystallised out (off-white needles m.p. 157–159° C., 36.3 g, 95.1%). δH (DMSO $d^6$) 8.5 (1H, d), 6.88 (2H, d), 6.49 (2H, d), 4.92 (2H, b,s), 4.38 (1H, s), 4.12 (2H, q), 4.07 (1H, m), 3.73 (2H, m), 3.58 (2H, m), 2.94 (1H, dd), 2.77 (1H, dd), 1.88 (2H, 2dd), 1.43 (1H, b,d), 1.31 (1H, b,d), 1.18 (3H, t).

INTERMEDIATE 12

2(S)-(2-Bromo-3-oxo-spiro[3.5]non-1-en-1-ylamino)-3-(4-nitrophenyl)propionic acid ethyl ester Powdered N-bromosuccinimide (4.98 g) was added portionwise to a stirred solution of the Intermediate 8 (10.3 g) in ethyl acetate (100 mL) at 20–25° C. over 90 minutes. After another 30 minutes, and following an LC completion check, the reaction was quenched by addition of sodium sulphite (0.5 g) in water (50 mL). The organic phase was then washed with water (2×50 mL), dried ($MgSO_4$), filtered and evaporated to give the product as an off-white foam (12.4 g, quantitative yield). $^1H$ NMR ($D_6$-DMSO) δ0.95–1.84 (10H, m); 1.28 (3H, t); 3.14 (1H, dd); 3.38 (1H, dd); 4.19 (2H, q); 4.85 (1H, m); 7.64 (2H, d); 8.20 (2H, d); 8.98 (1H (b)d) ppm. Mass Spectrum: ($ESI^+$) 451.1/453.1

INTERMEDIATE 13

3-(4-Amino-phenyl)-2(S)-(2-bromo-3-oxo-spiro[3.5]non-1-en-1-ylamino)propionic acid ethyl ester Method A Crude Intermediate 12 was re-dissolved in ethanol (100 mL) and the solution added to 50% wet, 5% palladium on charcoal (0.5 g). The resulting preparation was hydrogenated at atmospheric pressure at 20–25° C. until the theoretical volume of gas had been taken up and the reduction had been shown to be complete by LC. Following catalyst removal by filtration, the solvent was removed in vacuo to leave the product as an off-white foam (11.1 g, 95.3%).

Method B

Intermediate 8 (10 g) was dissolved in ethyl acetate (100 mL) and hydrogenated at 20–25° C., at atmospheric pressure, in the presence of 50% wet, 5% palladium on charcoal (0.5 g). Once the reduction was complete, the catalyst was filtered off and powdered N-bromosuccinimide (NBS, 4.1 g) added portion-wise to the liquors over 30 minutes. An in-process completion check showed 80% conversion to product. Further NBS (1.0 g) was added subsequently to consume all the starting material. The reaction was quenched with 1% sodium sulphite solution (50 mL), and the organic phase extracted with water (2×50 mL). The solid that precipitated during the last water wash was collected by filtration and dried in vacuo at 60° C. to afford the title compound (8.7 g, 74.9% yield, LC 98% PAR). Further product (1.22 g), along with the dibromo- and tribromo-analogues (0.72 g & 0.12 g respectively) were isolated after chromatography of the mother liquors (silica gel; 2–5% MeOH in DCM).

$^1H$ NMR ($D_6$-DMSO): δ1.02–1.88 (10H, m); 1.28 (3h, t); 2.89 (1H, dd); 3.08 (1h, dd); 4.20 (2H, q); 4.71 (1H, m); 5.01 (2H, (b)s); 6.53 (2H, d); 6.94 (2H, d); 8.94 (1H, (b)d) ppm. Mass Spectrum: ($ESI^+$) 421.1/423.1

INTERMEDIATE 14

4-Nitro-(S)-Phenylalanine Hydroxyethyl ester Hydrochloride

Dry hydrogen chloride (68.3 g) was dissolved in ethylene glycol (994 mL) at <20° C. and then solid 4-nitro-(S)-phenylalanine (198.7 g) added with stirring. The mixture was heated to 80–85° C. and held at this temperature for 2 h. After a LC completion check, the preparation was allowed to drift to 60° C. and seeded with authentic product. Once crystallisation had initiated, the resulting suspension was cooled further to 20° C. and stirred out overnight. The 4-nitro(S)-phenylalanine hydroxyethyl ester hydrochloride was collected by filtration, washed in situ with dimethoxyethane (795 mL), and then dried in vacuo at 40–45° C. to constant weight (white powder m.p. 195–197° C., 187.0 g, 73.9% yield). $^1H$ NMR ($D_6$-DMSO): δ3.27 (2H, ddd); 3.42 (2H, m); 4.01 (2H, m); 4.27 (1H, t); 4.88 (1H, b,s); 7.52 (2H, d); 8.11 (2H, d); 8.76 (3H, b,s) ppm. Mass Spectrum: $ESI^+$ (m/z+1) 255.0

INTERMEDIATE 15

3-(4-Nitrophenyl)-2(S)-(3-oxo-7-oxaspiro[3.5]non-1-en-1-ylamin))propionic acid hydroxy thyl ester Solid spiro[3,5]nonane-1,3-dione (70.0 g) was charged to a stirred suspension of Intermediate 14 (120.0 g) in ethyl acetate (1200 mL) containing triethylamine (64 mL) at 20–25° C. The whole was then boiled under reflux for 2 h and checked for completion (LC). Having established that the reaction had finished, the preparation was cooled to 20° C. and water (360 mL) added. 2M Hydrochloric acid (46 mL) was added subsequently to adjust the pH from 6 to 1.5. After removal of the aqueous phase, the organic layer was washed successively with 10% brine (330 mL), 5% sodium carbonate solution (250 mL), and 10% brine (2×330 mL), prior to being dried with magnesium sulphate. The solution was evaporated to dryness in vacuo to obtain the title compound as a clear, orange-brown gum (yield by LC assay 160.5 g, 94.1%). This intermediate was used directly in the next step. $^1H$ NMR ($D_6$-DMSO): δ1.07–1.70 (10H, b,m); 3.16 (1H, dd); 3.37 (1H, dd); 3.59 (2H, m); 4.14 (2H, t); 4.38 (1H,m); 4.40 (1H, s); 4.88 (1H, t); 7.46 (2H, d); 8.19 (2H, d); 8.38 (1H, d) ppm. Mass Spectrum: $ESI^+$ (m/z+1) 389

INTERMEDIATE 16

3-(4-Aminophenyl)-2(S)-(3-oxo-7-oxaspiro[3.5]non-1-en-1-ylamino)propionic acid hydroxyethyl ester Intermediate 15 (68.5 g) in ethyl acetate (350 mL) was hydrogenated at 5 Bar and <30° C. in the presence of 5% palladium on charcoal (61% wet) (3.4 g), until gas uptake ceased (circa 1 h). After filtering off the catalyst and washing the pad with ethyl acetate (2×100 mL), the combined organic solutions were evaporated to dryness in vacuo to furnish the title compound as a straw coloured foam, in essentially quantitative yield (63.2 g). $^1$H NMR ($D_6$-DMSO): δ1.08–1.79 (10H, b,m); 2.88 (1H, dd); 3.04 (1H, dd); 3.64 (2H m); 4.11 (1H, m); 4.18 (2H, m); 4.39 (1H, s); 4.89 (1H, t); 4.99 (1H, b,s); 6.53 (2h, d); 6.96 (2H, d); 8.33 (1H, d) ppm. Mass Spectrum: ESI$^+$ (m/z+1) 359.1

EXAMPLE 1

Ethyl 2(S)-[(3-oxospiro[3.5]non-1-en-1-yl)amino]-3-{4-[(3,5-dichloroisonicotinoyl)amino]phenyl}propanoate A solution of Intermediate 2 (3.1 g) in dichloromethane (DCM, 5 mL) was added dropwise to N-methyl morpholine (1.6 g) and Intermediate 9 (4.64 g) dissolved in DCM (40 mL) at 0–5° C. After stirring for 1 h, the organic phase was washed successively with 2M hydrochloric acid (10 mL), 10% sodium bicarbonate (10 mL) and saturated brine (10 mL), then dried (MgSO$_4$) and evaporated in vacuo, to leave a pale yellow powder (6.72 g). The crude product was purified by a hot reslurry in 2:1 ethyl acetate: methyl t-butyl ether (60 mL). The suspension was cooled, filtered, and the solid washed with 1:2 ethyl acetate: methyl t-butyl ether (2×30 mL). Dry title compound was obtained after drying in vacuo (5.26 g, 72.4% yield, m.p. 194° C.). δH (CDCl$_3$, 300K) 10.86 (1H, s), 8.78 (2H, s), 8.34 (1H, d, J 8.5 Hz), 7.56 (2H, d, J 8.5 Hz), 7.25 (2H, d, J 8.5 Hz), 4.36 (1H, s), 4.20–4.11 (3H, m), 3.13 (1H, dd, J 13.8, 5.3 Hz), 3.00 (1H, dd, J 9.2, 13.8 Hz), 1.67–1.19 (10H, m), 1.17 (3H, t, J 4.1 Hz); m/z(ES$^+$, 70V) 516.0 and 518.0 (MH$^+$).

EXAMPLE 2

Ethyl 2(S)-[(2-bromo-3-oxospiro[3.5]non-1-en-1-yl)amino]-3-{4-[(3,5-dichloroisonicotinoyl)amino]phenyl}propanoate A solution containing Example 1 (500 mg, 0.97 mmol) and triethylamine (2 eq, 270 μl) in THF (10 ml) at 0° was treated dropwise with a solution of bromine (1.1 eq, 170 mg) in THF (5 ml). After 20 mins the reaction was allowed to warm to room temperature prior to dilution with EtOAc (100 ml). The crude reaction mixture was washed with saturated aqueous NaHCO$_3$ (20 ml) and brine (20 ml), dried (MgSO$_4$) filtered and concentrated in vacuo. The residual foam was chromatographed (SiO$_2$; EtOAc) to give the title compound as a white powder (511 mg, 0.86 mmol, 95%). δH (CDCl$_3$, 300K) 8.48 (2H, s), 8.05 (1H, s br), 7.52 (2H, d J 8.4 Hz), 7.04 (2H, d J 8.5 Hz), 5.81 (1H, d br, J 8.3 Hz), 4.98–4.91 (1H, m), 4.21 (2H, q, J 7.1 Hz), 3.21 (2H, d J 5.3 Hz), 1.70–1.66 (4H, m), 1.53–1.44 (4H, m), 1.28 (3H, t J 7.1 Hz), 1.20–1.16 (2H, m); m/z (ES$^+$, 70V) 597.9 and 595.0 (MH$^+$).

EXAMPLE 3

2(S)-[(2-Bromo-3-oxospiro[3.5]non-1-en-1-yl)amino]3-{4-[(3,5-dichloroisonicotinoyl)amino]phenyl}propanoic acid The compound of Example 2 (511 mg, 0.86 mmol) in THF (5 ml) was treated in a single portion with LiOH.H$_2$O (50 mg, 1.19 mmol) in H$_2$O (1 ml) and the reaction stirred at room temperature for 2 h. The reaction was then quenched by the addition of HOAc (glacial, 1 ml) and the volatiles removed in vacuo. Water (10 ml) was then added to the residue to effect precipitation. The precipitate was collected by vacuum filtration and the residue washed with water (2×5 ml). Drying under vacuum gave the title compound as a fine white solid (421 mg, 0.74 mmol, 87%). δH (DMSO d$^6$, 390K) 10.34 (1H, s), 8.67 (2H, s), 7.53 (2H, s br), 7.26 (2H, d J 8.26 Hz), 4.67 (1H, m), 3.26–3.22 (1H, m), 3.13–3.08 (1H, m), 1.67–1.21 (10H, m); m/z (ES$^+$, 70V) 569.9 and 567.9 (MH$^+$).

EXAMPLE 4

Hydroxyethyl 2(S)-[(3-oxospiro[3.5]non-1-en-1-yl)amino]-3-{4-[(3.5-dichloroisonicotinoyl)amino]phenyl}propanoate Intermediate 2 (31.0 g) was introduced dropwise to a well-stirred solution of Intermediate 16 (50.0 g) in ethyl acetate (500 mL) and triethylamine (25 mL). The reaction temperature was kept below 25° C. throughout by external cooling. Acylation of the starting material was complete after a 1.5 hour stir-out. Water (150 mL) was charged at the end of this period, followed by sufficient 2M hydrochloric acid to lower the pH to 1–1.5. Following separation, the organic phase was washed with water (2×150 mL), 5% sodium carbonate solution (150 mL) and 10% brine (2×150 mL) then dried (MgSO$_4$), filtered and evaporated in vacuo to afford the title compound as a yellow-brown foam (71.1 g, 95.6% yield). $^1$H NMR D$_6$-DMSO: δ1.1–1.73 (10H, b,m); 2.98 (1H, dd); 3.20 (1H, dd); 3.64 (2H, m); 4.13 (2H, t); 4.24 (1H, m); 4.39 (1H, s); 4.87 (1H, t); 7.28 (2H, d); 7.59 (2H, d); 8.37 (1H, d); 8.81 (2H, s); 10.88 (1H, s) ppm. Mass Spectrum: ESI$^+$ m/z 532/534

EXAMPLE 5

2-Hydroxyethyl 2(S)-(2-bromo-3-oxo-spiro[3.5]non-1-n-1-ylamino)-3-{4-[(3,5-dichloroisonicotinoyl)amino]phenyl}propanoate Method A To a solution of the compound of Example 3 (0.5 g, 0.89 mmol) in DMF (2 ml) was added EDC (190 mg, 0.97 mmol), HOBT (140 mg, 1.03 mmol) and ethylene glycol (2.5 ml). The mixture was stirred at room temperature for 48 h then partitioned between EtOAc (15 ml) and water (10 ml). The aqueous layer was separated and the organics washed with water (3×5 ml), brine (10 ml), dried (Na$_2$SO$_4$), filtered and concentrated in vacuo to give a crude solid. The crude was chromatographed (SiO$_2$; EtOAc) to give the title compound as a white powder (287 mg, 53%). δH (300 MHz, DMSO d$^6$) 8.88 (1H, d, J 9.2 Hz), 8.79 (2H, s), 7.59 (1H, d, J 8.5 Hz), 7.26 (2H, d, J 8.5 Hz), 4.86 (1H, m), 3.62 (1H, m), 3.25 (1H, dd, J 14.0, 4.6 Hz), 3.04 (1H, dd, J 14.0, 9.4 Hz), 1.58–1.79 (6H, m), 1.37 (1H, d, J 12.7 Hz), 1.11 (2H, br).

Method B

Powdered N-bromosuccinimide (19.3 g) was added portionwise to a solution of Example 4 (60.7 g) in ethyl acetate (610 mL) at 0–5° C. over 2 h. LC monitoring was used to check reaction progress and suppress over-bromination of the starting material. Upon completion, the reaction was quenched with a solution of sodium sulphite (3.0 g) in water (60 mL). The organic phase was washed with water (2×100 mL), and then concentrated to give a 25% w/v solution of the product, with concomitant azeo-drying, by distillation at atmospheric pressure. The product began to crystallise out towards the end of the step. After cooling to 20° C. over 2 h, and stirring overnight, the resulting suspension was filtered and the solid washed with cold (0–5° C.) ethyl acetate (2×80 mL). The title compound was thus obtained as a fawn microcrystalline powder after drying to constant weight at 70° C. in vacuo (m.p. 210–212° C., 63.2 g, 90.6% yield). $^1$H NMR D$_6$-DMSO: δ1.05–1.78 (10H, b,m); 3.04 (1H, dd); 3.25 (1H, dd); 3.66 (2H, m); 4.19 (2H, t); 4.84 (1H, m); 4.90 (1H, t); 7.28 (2H, d); 7.59 (2H, d); 8.80 (2H, s); 8.92 (1H, d); 10.92 (1H, s) ppm. Mass Spectrum: ESI$^+$ (m/z+1) 612.0

EXAMPLE 6a

Ethyl-3-[4-([2,7]naphthyridin-1-ylamino)phenyl]-2 (S)-(3-oxos-piro[3.5]non-1-en-1-ylamino) propanoate, di-(4-toluoyl)-2(R),3(R)-tartaric acid salt Intermediate 5 (35.6 g) was charged to a solution of Intermediate 9 (81.6 g) in absolute ethanol (727 mL). Ethanolic hydrogen chloride, prepared in a preliminary step by adding acetyl chloride (1.5 mL) dropwise to chilled ethanol (89 mL), was then introduced, and the resulting mixture heated to 40° C. for 16 h under nitrogen. The reaction was quenched with triethylamine (36 mL) and then solvent swapped to solution in ethyl acetate (820 mL) by distillation at atmospheric pressure. After cooling to ambient temperature, the ester solution was washed with 15% brine (3×400 mL) prior to azeo-drying. Whilst at reflux, a solution of di-(4-toluoyl)-2(R), 3(R)-tartaric acid (92.1 g) in ethyl acetate (440 mL) was added, the preparation brought off the boil, seeded, and then cooled to 20° C. over 12 h. The title compound was filtered off, washed with ethyl acetate (2×220 mL), and subsequently dried in vacuo at 45° C. to give granular yellow solid (156.2 g, 76.5% yield). $^1$H NMR (D$_6$-DMSO): δ1.22 (1H, m); 1.28 (3H, t); 1.47–1.84 (9H, b,m); 2.48 (6H, s); 3.07 (1H, dd); 3.24 (1H, dd); 4.26 (2H, q); 4.28 (1H, m); 4.45 (1H, s); 5.92 (2H, s); 7.22 (1H, d); 7.31 (2H, d); 7.50 (4H, d); 7.78 (1H, d); 7.87 (2H, d); 7.99 (4H, d); 8.28 (1H, d); 8.51 (1H, d); 8.76 (1H, d); 9.64 (1H, b,s); 9.93 (1H, s) ppm

EXAMPLE 6b

Ethyl-3-[4-([2,7]naphthyridin-1-ylamino)phenyl]-2 (S)-(3-oxo-spiro[3.5]non-1-en-1-ylamino) propanoate, oxalate salt A solution of Intermediate 8 (20.0 g) in ethanol (80 ml) was hydrogenated over 5% w/w Pd/C, ca. 50% wet (2.5% w/w dry) at ca. 50 psi until hydrogen uptake ceased. The mixture was filtered, washing with ethanol (60 ml). To this solution was added Intermediate 5 (8.04 g) and a solution of acetyl chloride (0.383 g) in ethanol (15 ml) and the mixture heated at 60° C. for 3.5 h. The solution was cooled to 20° C. and triethylamine (5.93 g) added. The turbid solution was then filtered, washing with ethanol (10 ml) and a solution of oxalic acid (4.62 g) in ethanol (15 ml) added followed by seeds of Intermediate 5 oxalate salt. When crystallisation was complete the mixture was filtered, washing with ethanol (20 ml) to give the title compound as a yellow solid,14.7 g, 53.6%. C, 63.72%; H, 5.71%; N, 9.88%. C$_{30}$H$_{32}$N$_4$O$_7$ requires C, 64.26%; H, 5.76%; N, 10.00%. $^1$H NMR, DMSO-d$^6$, δ1.2 (3H, t), 1.4–1.7 (10H, m), 3.0 (1H, dd), 3.15 (1H, dd), 3.9–4.9 (2H, broad), 4.15 (3H, m), 4.35 (1H, s), 7.10 (1H, d), 7.20 (2H, d), 7.70 (1H, d), 7.75 (2H, d), 8.15 (1H, d), 8.40 (1H, d), 8.65 (1H, d), 9.5–9.8 (1H, broad), 9.95 (1H, s).

EXAMPLE 7

Ethyl-3-[4-([2,7]naphthyridin-1-ylamino)phenyl]-2 (S)-(3-oxo-spiro[3.5]non-1-en-1-ylamino)propanoate Intermediate 5 (24.3 g) and Intermediate 9 (45.8 g) were suspended in ethanol (300 mL) and heated to 60° C. for 4 h, under nitrogen. Ethanol was removed in vacuo and the residue taken up in ethyl acetate (350 mL). The latter solution was washed carefully with a solution of potassium carbonate (10.4 g) in water (100 mL), followed by saturated brine (100 mL). The ethyl acetate solution was evaporated to dryness under vacuum, and the residue purified by column chromatography on silica, eluting with 10% ethanol in ethyl acetate, to give the title compound as an orange-yellow foam (56.9 g, 90.4% yield). δH (CDCl$_3$) 9.61 (1H, s), 8.65 (1H, d, J 5.7 Hz), 8.25 (1H, d, J 5.8 Hz), 7.71 (2H, d, J 8.4 Hz), 7.63 (1H, d, J 8.5 Hz), 7.12 (2H, d, J 8.5 Hz), 7.05 (1H, d, J 5,8 Hz), 5,80 (1H, m), 4.55 (1H, s), 4,29 (2H, q, J 7.2 Hz), 3.13 (2H, m), 1.87–1.25 (14H, m); m/z (ES$^+$, 70V) 471.1 (MH$^+$).

EXAMPLE 8

Ethyl 2(S)-(2-bromo-3-oxo-spiro[3.5]non-1-en-1-ylamino)-3-[4-([2,7]naphthyridin-1-ylamino)phenyl] propanoate Method A A stirred solution of the compound of Example 7 (300 mg, 0.637 mmol) and triethylamine (1.2 eq, 100 µl) in THF (10 ml) at 0° was treated dropwise with a solution of bromine in DCM (2% v/v, 2.1 ml, 1.2 eq). After 12 h the reaction was diluted with DCM (50 ml) and washed successively with saturated aqueous NaHCO$_3$, dried (MgSO$_4$) filtered and concentrated in vacuo. The residual foam was triturated with diisopropylether and the resulting solid collected and dried in vacuo to give the title compound as a pale yellow powder (0.45 mmol, 76%).

Method B

A suspension of Example 6a (250 g) in ethyl acetate (1500 mL) was stirred with 10% aqueous potassium carbonate (545 mL) to give an organic solution of Example 7. The latter was washed with water (250 mL) and 15% brine (250 mL) then cooled to −10° C. in the reaction vessel. N-Bromosuccinimide (51.4 g) was added portionwise to the solution over 1 h at −10 to −5° C. Once all the reagent had been charged, the preparation was warmed to 40° C. over 1 h then kept at this temperature for another 2 h. Reaction progress was closely monitored by HPLC. As soon as Example 7 had all been consumed, the halogenation was quenched with 2% aqueous sodium sulphite (200 mL). The organic phase was washed with water (250 mL) and saturated brine (250 mL) prior to a polish filtration. Wet ethyl acetate was then distilled out to leave a dry 25% w/v solution of the product. The concentrate was seeded just below boiling, and diluted slowly with n-heptane (963 mL), once crystal growth had become apparent. Further crystallisation occurred during cooling to 20° C. over 4 h. Filtration of the resulting slurry afforded the title compound which was washed with 2:1 heptane: ethyl acetate (150 mL) and heptane (150 mL) before being dried in vacuo at 40–45° C. (m.p. 192.5–195° C., 147.8 g, 92.3%).

Method C

Intermediate 13 (14.4 g), Intermediate 5 (6.47 g) and absolute ethanol (140 mL) were heated to 40–45° C. and stirred out under nitrogen. LC monitoring showed the reaction to be complete after 12 h, whereupon triethylamine (10 mL) was added and the mixture stirred for 0.5 h. After removal of solvent in vacuo (40–50° C./50–100 mBar), the residual orange-red paste (31.1 g) was partitioned between ethyl acetate (150 mL) and water (100 mL). The aqueous phase was back-extracted with ethyl acetate (50 mL) and then the combined organic layers were distilled at atmospheric pressure to leave 3 volumes solvent with respect to the theoretical yield of product. The concentrated solution was seeded at 75° C. and then heptane (140 mL) added via a syringe pump over 2 h, whilst maintaining this temperature. With most of the product crystallised, the mixture was cooled to 20° C. and held for 1 h prior to filtration. Following heptane washes (2×50 mL) and drying at 60° C. to constant weight, the crude product was obtained as a pale orange solid [17.9 g, 95.1% yield; LC 93.8% PAR, 91.2% w/w assay (versus an analytical specimen)=>86.7% active ingredient yield].

δH (CDCl$_3$) 9.81 (1H, s), 8.64 (1H, d, J 5.7 Hz), 8.29 (1H, d, J 5.8 Hz), 7.75 (2H, d, J 8.3 Hz), 7.60 (1H, d, J 5.8 Hz), 7.12 (2H, d, J 8.4 Hz), 7.08 (1H, d, J 5.7 Hz), 5.91 (1H, m), 5.03 (1H, m), 4.28 (2H, q, J 7.1 Hz), 3.29 (2H, m), 1.81–1.39 (10H, m), 1.35 (3H, t, J 7.1 Hz); m/z(ES$^+$, 70V) 550.0 (MH$^+$).

EXAMPLE 9

Ethyl 3-[4-([2,7]naphthyridin-1-ylamino)phenyl]-2 (S)-[(3-oxo-7-oxa-spiro[3.5]non-1-en-1-yl)amino]propanoate Acetyl chloride (1 mL) was added cautiously to stirred ethanol (50 mL) with exclusion of moisture. This solution was then added to a stirred suspension of the Intermediate 11 (24.0 g) and Intermediate 5 (12.0 g) in ethanol (200 mL) and the whole heated to 60° C. under nitrogen for 2 h. Ethanol was removed in vacuo and the residue taken up in ethyl acetate (300 mL). The latter solution was washed with 5% sodium hydroxide solution (100 mL) followed by water (2×50 mL). Some tarry material was cut away with the aqueous phases. The organic phase was dried (Na$_2$SO$_4$) and its volume reduced to approximately 100 mL, crystallisation of the product occurred after seeding. After stirring out at 0–5° C. for 1 h the title compound was isolated and dried at 50° C. in vacuo (28.2 g, pale yellow solid m.p. 112° C., 85.6% yield). δH (DMSO d$^6$) 10.02 (1H, s), 9.73 (1H, s), 8.78 (1H, d), 8.33 (1H, d), 7.98 (2H, d), 7.89 (1H, d), 7.44 (2H, d), 7.32 (1H, d), 4.61 (1H, s), 4.42 (1H, m), 4.36 (2H, q), 3.94 (2H, m), 3.80 (2H, m), 3.34 (1H, dd), 3.17 (1H, dd), 2.11 (2H, m), 1.69 (1H, d), 1.58 (1H, d), 1.40 (3H, t). ESI$^+$ (m/z+1) 473.3

EXAMPLE 10

Ethyl 2(S)-[(2-isopropylsulfanyl-3-oxo-7-oxa-spiro[3.5]non-1-en-1-yl)amino]-3-[4-([2,7]naphthyridin-1-ylamino)phenyl]propanoate Sulphuryl chloride (13.6 g) was added drop-wise to diisopropyl disulphide (25.0 g) in tetrahydrofuran (THF, 150 mL) at 0–5° C. under nitrogen. After stirring out for 30 minutes, the resulting isopropyl sulphenyl chloride preparation was introduced slowly, from a graduated dropping funnel, to a solution of Example 9 (30.0 g) in THF (500 mL), held at the same temperature. Conversion to product was complete after 85 mL of the stock solution had been charged. The reaction was quenched with 10% sodium bicarbonate solution (175 mL) and the layers separated. The aqueous phase was extracted with ethyl acetate (100 mL), and the combined organic solutions then washed with saturated brine (100 mL). The isolated organic phase was solvent swapped to ethanol (650 mL), by distillation at atmospheric pressure, from which the product crystallised on cooling. This suspension was filtered at 20° C. and the title compound washed with ethanol (2×30 mL) prior to drying in vacuo at 50–60° C. (26.9 g; 77.5% yield, off-white powder m.p. 221° C.). δH (DMSO d$^6$, 390K) 9.83 (1H, s), 9.52 (1H, s), 8.94 (1H, d, J 9.5 Hz), 8.65 (1H, d, J 5.6 Hz), 8.15 (1H, d, J 5.7 Hz), 7.78 (2H, d, J 8.5 Hz), 7.68 (1H, d, J 5.6 Hz), 7.23 (2H, d, J 8.5 Hz), 7.12 (1H, d, J 5.7 Hz), 5.26 (1H, m), 4.19 (2H, q, J 7.1 Hz), 3.81–3.76 (2H, m), 3.64–3.55 (2H, m), 3.20 (1H, dd, J 13.8, 4.3 Hz), 2.96 (1H, dd, J 13.8, 10.3 Hz), 2.81–2.74 (1H, m), 2.06–1.93 (2H, m), 1.50–1.47 (1H, m), 1.32–1.28 (1H, m), 1.23 (3H, t, J 7.1 Hz), 1.07 (3H, d, J 6.6 Hz), 1.05 (3H, d, J 6.6 Hz); m/z (ES$^+$, 70V) 547.2 (MH$^+$).

What is claimed is:

1. A process for the preparation of a compound of formula 1):

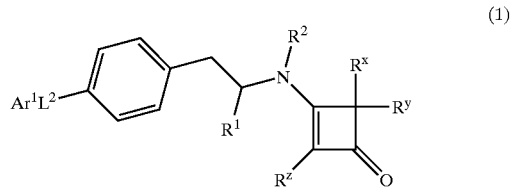

wherein:
Ar$^1$ is an optionally substituted aromatic or heteroaromatic group;

L$^2$ is a linker group selected from —N(R$^4$)—, —CON(R$^4$)— and —S(O)$_2$N(R$^4$)—;

R$^4$ is a hydrogen atom or an a optionally substituted straight or branched C$_{1-6}$alkyl group;

R$^1$ is a carboxylic acid (—CO$_2$H) or an acyclic or cyclic carboxylic acid ester, an amide, tetrazole, phosphonic acid, phosphinic acid, sulphonic acid, sulphinic acid, boronic acid, or an acylsulphonamide group;

R$^2$ is a hydrogen atom or a C$_{1-6}$alkyl group;

R$^x$, R$^y$ and R$^z$, which may be the same or different, are each -L$^1$(Alk$^1$)$_n$(R$^3$)$_v$, or R$^z$ is -L$^1$(Alk$^1$)$_n$(R$^3$)$_v$ and R$^x$ and R$^y$ are joined together to form an optionally substituted spiro linked cycloaliphatic or heterocycloaliphatic group;

L$^1$ is a covalent bond or —O—, —S—, or —Se— atom or an —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— group;

R$^8$ is a hydrogen atom or optionally substituted straight or branched C$_{1-6}$alkyl group;

Alk$^1$ is an optionally substituted aliphatic chain or an optionally substituted heteroaliphatic chain containing one to four —O— or —S— atoms or —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— groups that interrupt or are at the terminus of the aliphatic chain;

R$^3$ is a hydrogen or halogen atom or group selected from —OR$^{3a}$, —SR$^{3a}$, —CN and an optionally substituted cycloaliphatic, heterocycloahiphatic, polycycloaliphatic, heteropolycycloaliphatic, aromatic or heteroaromatic group;

R$^{3a}$ is hydrogen atom or an optionally substituted straight or branched C$_{1-6}$alkyl group or C$_{3-8}$cycloalkyl group;

n is zero or the integer 1; and v is the integer 1, 2 or 3;

provided that when n is zero and $L^1$ is a covalent bond, v is the integer 1;

and the salts, solvates, hydrates and N-oxides thereof; which comprises reacting a compound of formula (2):

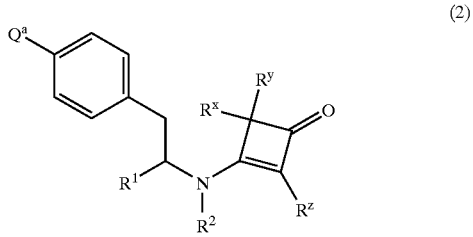

(2)

wherein:

$Q^a$ is a group —N($R^4$)H;

and the salts, solvates, hydrates and N-oxides thereof;

with a compound $Ar^1W$ wherein

W is a group selected from $X^1$, —$COX^2$ and —$SO_2X^3$;

$X^1$ is a leaving atom or group;

$X^2$ is a halogen atom or a —OH group; and $X^3$ is a halogen atom.

2. A process according to claim 1 wherein the reaction is carried out in a solvent in the presence of an acid when W is the group $X^1$.

3. A process according to claim 2 wherein the solvent is selected from an alcohol, ether, acetic acid, water, acetonitrile, substituted amide or ester.

4. A process according to claim 2 wherein the reaction is carried out in an alcohol in the presence of an acid catalyst.

5. A process according to claim 1 wherein the reaction is carried out in the presence of a base, an organic amine or a cyclic amine and an organic solvent when W is the group $COX^2$ and $X^2$ is a halogen atom.

6. A process according to claim 5 wherein the organic solvent is selected from a halogenated hydrocarbon, a dipolar aprotic solvent, an ether or an ester.

7. A process according to claim 1 wherein the reaction is carried out in the presence of a condensing agent and a halogenated hydrocarbon, dipolar aprotic or an ether solvent when W is the group $CO_2H$.

8. A process according to claim 1 wherein the reaction is carried out in the presence of a base, an organic amine or a cyclic amine and a halogenated hydrocarbon, dipolar aprotic or an ether solvent when W is the group $SO_2X^3$.

9. A process according to any one of claim 1 wherein the compound of formula (2) is prepared by reduction of a compound of formula (4):

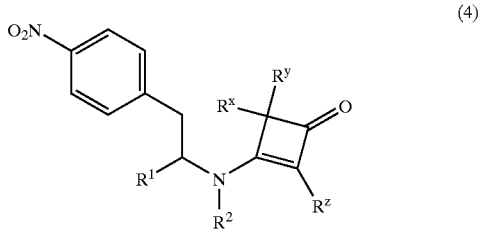

(4)

10. A process according to claim 9 wherein the reduction is carried out by catalytic hydrogenation or by chemical reduction.

11. A process according to claim 1 wherein $R^4$ is a hydrogen atom.

12. A process according to claim 9 wherein the compound of formula (4) is prepared by reaction of a compound of formula (5):

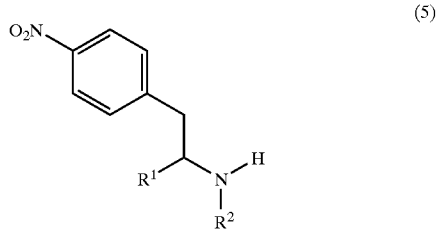

(5)

with a compound of formula (6a) or (6b):

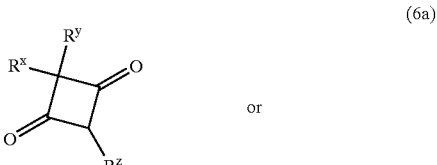

(6a)

or

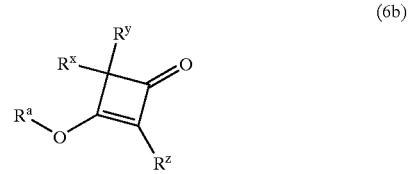

(6b)

wherein $R^a$ represents a $C_{1-6}$alkyl group or a silyl group.

13. A process according to claim 12 wherein the reaction is carried out in the presence of an organic solvent.

14. A process according to claim 13 wherein the solvent is selected from an aromatic hydrocarbon, a halogenated hydrocarbon or an ester.

15. A process according to claim 1 wherein $R^1$ is the group —$CO_2Alk^7$; and $Alk^7$ is a straight or branched optionally substituted $C_{1-8}$alkyl group, an optionally substituted $C_{2-8}$alkenyl group, an optionally substituted $C_{2-8}$alkynyl group, an optionally substituted $C_{3-8}$cycloalkyl group, an optionally substituted $C_{3-8}$heterocycloalkyl group, an optionally substituted $C_{3-8}$cycloalkylC$_{1-8}$alkyl group, an optionally substituted $C_{3-8}$heterocycloalkylC$_{1-8}$alkyl group, an optionally substituted $C_{1-6}$alkyloxyC$_{1-6}$alkyl group, an optionally substituted hydroxyC$_{1-6}$alkyl group, an optionally substituted $C_{1-6}$alkylthioC$_{1-6}$alkyl group, an optionally substituted $C_{1-6}$alkylsulfinylC$_{1-6}$alkyl group, an optionally substituted $C_{1-6}$alkylsulfonylC$_{1-6}$alkyl group, an optionally substituted $C_{3-8}$cycloalkyloxy C$_{1-6}$alkyl group, an optionally substituted $C_{3-8}$cycloalkylthioC$_{1-6}$alkyl group, an optionally substituted $C_{3-8}$cycloalkylsulfinylC$_{1-6}$alkyl group, an optionally substituted $C_{3-8}$cycloalkylsulfonylC$_{1-6}$alkyl group, an optionally substituted $C_{1-6}$alkyloxycarbonylC$_{1-6}$alkyl group, an optionally substituted $C_{1-6}$alkyloxycarbonylC$_{1-6}$alkenyl group, an optionally substituted $C_{1-6}$alkyloxycarbonyloxyC$_{1-6}$alkyl group, an optionally substituted $C_{1-6}$alkyloxycarbonyloxyC$_{1-6}$alkenyl group, an optionally substituted $C_{3-8}$cycloalkyloxycarbonyloxyC$_{1-6}$alkyl group, an optionally substituted N-di-C$_{1-8}$alkylaminoC$_{1-8}$alkyl group, an optionally substituted N—C$_{6-12}$aryl-N—C$_{1-6}$alkylaminoC$_{1-6}$alkyl group, an optionally substituted N-di-C$_{1-8}$alkyl-carbamoylC$_{1-8}$alkyl group, an optionally substituted C$_{6-12}$arylC$_{1-6}$alkyl group, an optionally substituted heteroC$_{6-10}$arylC$_{1-6}$alkyl group, an optionally substituted C$_{6-12}$aryl group, an optionally substituted C$_{6-12}$aryloxyC$_{1-8}$alkyl group, an optionally substituted C$_{6-12}$arylthioC$_{1-8}$alkyl group, an optionally substituted C$_{6-12}$arylsulfinylC$_{1-8}$alkyl group, an optionally substituted C$_{6-12}$arylsulfonylC$_{1-8}$alkyl group, an optionally substituted C$_{1-8}$alkanoyloxyC$_{1-8}$alkyl group, an optionally substituted C$_{4-8}$imidoC$_{1-8}$group, an optionally substituted C$_{6-12}$aroyloxyC$_{1-8}$alkyl group, or a triglyceride.

16. A process according to claim 1 which comprises hydrolysing a compound of formula (1) in which R$^1$ is —CO$_2$Alk$^7$ and Alk$^7$ is a straight or branched optionally substituted C$_{1-8}$alkyl group, an optionally substitute C$_{2-8}$alkenyl group, an optionally substituted C$_{2-8}$alkynyl group, an optionally substituted C$_{3-8}$cycloalkyl group, an optionally substituted C$_{3-8}$heterocycloalkyl group, an optionailly substituted C$_{3-8}$cycloalkylC$_{1-8}$alkyl group, an optionally substituted C$_{3-8}$heterocycloalkylC$_{1-8}$alkyl group, an optionally substituted C$_{1-6}$alkyloxyC$_{1-6}$alkyl group, an optionally substituted hydroxyC$_{1-6}$alkyl group, an optionally substituted C$_{1-6}$alkylthioC$_{1-6}$ group, an optionally substituted C$_{1-6}$alkylsulfinylC$_{1-6}$alkyl group, an optionally substituted C$_{1-6}$alkylsulfonylC$_{1-6}$alkyl group, an optionally substituted C$_{3-8}$cycloalkyloxyC$_{1-6}$alkyl group, an optionally substituted C$_{3-8}$cycloalkylthioC$_{1-6}$alkyl group, an optionally substituted C$_{3-8}$cycloalkylsulfinylC$_{1-6}$alkyl group, an optionally substituted C$_{3-8}$cycloalkylsulfonylC$_{1-6}$alkyl group, an optionally substituted C$_{1-6}$akyloxycarbonylC$_{1-6}$ alkyl group, an optionally substituted C$_{1-6}$alkyloxycarbonylC$_{1-6}$alkenyl group, an optionally substitut C$_{1-6}$alkyloxycarbonyloxyC$_{1-6}$alkyl group, an optionally substituted C$_{1-6}$alkyloxycarbonyloxyC$_{1-6}$alkenyl group, an optionally substituted C$_{3-8}$cycloalkyloxycarbonyloxyC$_{1-6}$alkyl group, an optionally substituted N-di-C$_{1-8}$alkylaminoC$_{1-8}$alkyl group, an optionally substituted N—C$_{6-12}$aryl-N—C$_{1-6}$alkylaminoC$_{1-6}$alkyl group, an optionally substituted N-di-C$_{1-8}$alkyl-carbamoylC$_{1-8}$alkyl group, an optionally substituted C$_{6-12}$arylC$_{1-6}$alkyl group, an optionally substituted heteroC$_{6-10}$arylC$_{1-6}$alkyl group, an optionally substituted C$_{6-12}$aryl group, an optionally substituted C$_{6-12}$aryloxyC$_{1-8}$alkyl group, an optionally substituted C$_{6-12}$arylthioC$_{1-8}$alkyl group, an optionally substituted C$_{6-12}$arylsulfinylC$_{1-8}$alkyl group, an optionally substituted C$_{6-12}$arylsulfonylC$_{1-8}$alkyl group, an optionally substituted C$_{1-8}$alkanoyloxyC$_{1-8}$alkyl group, an optionally substituted C$_{4-8}$imidoC$_{1-8}$alkyl group, an optionally substituted C$_{6-12}$aroyloxyC$_{1-8}$alkyl group, or a triglyceride.

to produce a compound of formula (1) in which R$^1$ is —CO$_2$H.

17. A process according to claim 1 which comprises esterifying a compound of formula (1) in which R$^1$ is —CO$_2$H to produce a compound of formula (1) in which R$^1$ is —CO$_2$Alk$^7$ and Alk$^7$ is a straight or branched optionally substituted C$_{1-8}$alkyl group, an optionally substituted C$_{2-8}$alkenyl group, an optionally substituted C$_{2-8}$alkynyl group, an optionally substituted C$_{3-8}$cycloalkyl group, an optionally substituted C$_{3-8}$heterocycloalkyl group, an optionally substituted C$_{3-8}$cycloalkylC$_{1-8}$alkyl group, an optionally substituted C$_{3-8}$hetrocycloalkylyC$_{1-8}$alkyl group, an optionally susbstituted C$_{1-6}$alkyloxyC$_{1-6}$alkyl group, an optionally substituted hydroxyC$_{1-6}$alkyl group, an optionally substituted C$_{1-6}$alkyltyhioC$_{1-6}$alkyl group, an optionally substituted C$_{1-6}$alkylsulfinylC$_{1-6}$alkyl group, an optionally substituted C$_{1-6}$alkylsulfonylC$_{1-6}$alkyl group, an optionally substituted C$_{3-8}$cycloalkyloxyC$_{1-6}$alkyl group, an optionally substituted C$_{3-8}$cycloalkylthioC$_{1-6}$alkyl group, an optionally substituted C$_{3-8}$cycloalkylsulfinylC$_{1-6}$alkyl group, an optionally substituted C$_{3-8}$cycloalkylsulfonylC$_{1-6}$alkyl group, an optionally substituted C$_{1-6}$alkyloxycarbonylC$_{1-6}$alkyl group, an optionally substituted C$_{1-6}$alkyloxycarbonylC$_{1-6}$alkenyl group, an optionally substituted C$_{1-6}$alkyloxycarbonyloxyC$_{1-6}$alkyl group, an optionally substituted C$_{1-6}$alkyloxycarbonyloxyC$_{1-6}$alkenyl group, an optionally substituted C$_{3-8}$cycloalkyloxycarbonyloxyC$_{1-6}$alkyl group, an optionally substituted N-di-C$_{1-8}$alkylaminoC$_{1-8}$alkyl group, an optionally substituted N—C$_{6-12}$aryl-N—C$_{1-6}$alkylaminoC$_{1-6}$ alkyl group, an optionally substituted N-di-C$_{1-8}$alkyl-carbamoylC$_{1-8}$alkyl group, an optionally substituted C$_{6-12}$arylC$_{1-6}$alkyl group, an optionally substituted heteroC$_{6-10}$arylC$_{1-6}$alkyl group, an optionally substituted C$_{6-12}$aryl group, an optionally substituted C$_{6-12}$aryloxyC$_{1-8}$alkyl group, an optionally substituted C$_{6-12}$arylthioC$_{1-8}$alkyl group, an optionally substituted C$_{6-12}$arylsulfinylC$_{1-8}$alkyl group, an optionally substituted C$_{6-12}$arylsulfonylC$_{1-8}$alkyl group, an optionally substituted C$_{1-8}$alkanoyloxyC$_{1-8}$alkyl group, an optionallly substituted C$_{4-8}$imidoC$_{1-8}$alkyl group, an optionally substituted C$_{6-12}$aroyloxyC$_{1-8}$alkyl group, or a triglyceride.

18. A process according to claim 1 for the preparation of compounds of formula (1b):

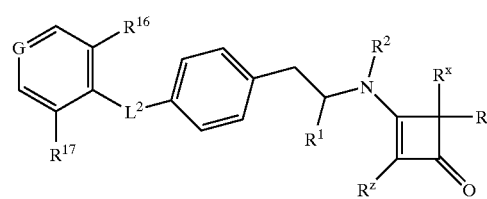

(1b)

wherein

—G= is —CR$^{18}$=, —N= or 13 N(O)=;

R$^{16}$, R$^{17}$ and R$^{18}$, which may be the same of different, are each a hydrogen atom or -L$^3$(Alk$^2$)$_t$L$^4$(R$^5$)$_u$;

L$^3$ and L$^4$ are, independently, a covalent bond, an —O— or —S— atom, or a —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— group;

R$^8$ is a hydrogen atom or an optionally substituted straight or branched C$_{1-6}$alkyl group;

t is zero or the interger 1;

u is an interger 1, 2 or 3;

Alk$^2$ is an optionally substituted aliphatic chain or an optionally substituted heteroaliphatic chain containing one to four —O— or —S— atoms or —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— groups that interrupt or are at the terminus of the aliphatic chain;

$R^5$ is a hydrogen or halogen atom or an optionally substituted $C_{1-6}$alkyl, optionally substituted $C_{3-8}$cycloalkyl, —$OR^6$, —$SR^6$, —$NR^6R^7$, —$NO_2$, —CN, —$CO_2R^6$, —$SO_3H$, —$SOR^6$, —$SO_2R^6$, —$SO_3R^6$, —$OCO_2R^6$, —$CONR^6R^7$, —$OCONR^6R^7$, —$CSNR^6R^7$, —$COR^6$, —$OCOR^6$, —$N(R^6)COR^7$, —$N(R^6)CSR^7$, —$SO_2N(R^6)(R^7)$, —$N(R^6)SO_2R^7$, $N(R^6)CON(R^7)(R^{19})$, —$N(R^6)CSN(R^7)(R^{19})$, or —$N(R^6)SO_2N(R^7)(R^{19})$ group; and $R^6$, $R^7$, and $R^{19}$ are, independently, a hydrogen atom or an optionally substituted $C_{1-6}$alkyl or $C_{3-8}$cycloalkyl group;

provided that when t is zero and each of the $L^3$ and $L^4$ is a covalent bond, then u is the integer 1 and $R^5$ is other than a hydrogen atom; and the salts, solvates, hydrates and N-oxides thereof.

19. A process according to claim 1 for the preparation of compounds of formula (1d):

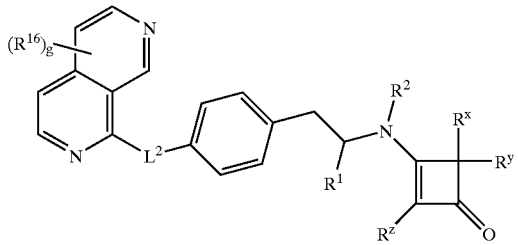

(1d)

wherein g is the integer 1, 2, 3 or 4;

$R^{16}$ is -$L^3(Alk^2)_tL^4(R^5)_u$;

$L^3$ and $L^4$ are, independently, a covalent bond, an —O— or —S— atom, or a —C(O)—, —C(O)O—, —OC(O)—, —C(S)—, —S(O)—, —S(O)$_2$—, —N($R^8$)—, —CON($R^8$)—, —OC(O)N($R^8$)—, —CSN($R^8$), —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$)SO$_2$N($R^8$)— group;

$R^8$ is a hydrogen atom or an optionally substituted straight or branched $C_{1-6}$alkyl group;

t is zero or the integer 1;

u is an integer 1, 2 or 3;

$Alk^2$ is an optionally substituted aliphatic chain or an optionally substituted heteroaliphatic chain containing one to four —O— or —S— atoms or —C(O)—, —C(O)O—, —OC(O)—, —C(S)—, —S(O)—, —S(O)$_2$—, —N($R^8$)—, —CON($R^8$)—, —OC(O)N($R^8$)—, —CSN($R^8$), —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$)SO$_2$N($R^8$)— groups that interrupt or are at the terminus of the aliphatic chain;

$R^5$ is a hydrogen or halogen atom or an optionally substituted $C_{1-6}$alkyl, optionally substituted ($C_{3-8}$cycloalkyl, —$OR^6$, —$SR^6$, —$NR^6R^7$, —$NO_2$, —CN, —$CO_2R^6$, —$SO_3H$, —$SOR^6$, —$SO_2R^6$, —$SO_3R^6$, —$OCO_2R^6$, —$CONR^6R^7$, —$OCONR^6R^7$, —$CSNR^6R^7$, —$COR^6$, —$OCOR^6$, —$N(R^6)COR^7$, —$N(R^6)CSR^7$, —$SO_2N(R^6)(R^7)$, —$N(R^6)SO_2R^7$, $N(R^6)CON(R^7)(R^{19})$ —$N(R^6)CSN(R^7)(R^{19})$, or —$N(R^6)SO_2N(R^7)(R^{19})$ group; and $R^6$, $R^7$, and $R^{19}$ are, independently, a hydrogen atom or an optionally substituted $C_{1-6}$alkyl or $C_{3-8}$cycloalkyl group;

provided that when t is zero and each of $L^3$ and $L^4$ is a covalent bond, then u is the integer 1 and $R^5$ is other than a hydrogen atom; and the salts, solvates, hydrates and N-oxides thereof.

20. A process according to claim 1 for the preparation of:

ethyl (2S)-2-[(2-bromo-3-oxospiro[3.5]non-1-en-1-yl)amino]-3-{4-[(3,5-dichloroisonicotinoyl)amino]phenyl}propanoate;

and the salts, solvates, hydrates and N-oxides thereof.

21. A process according to any one of the preceding claim 1 for the preparation of:

ethyl (2S)-2-(2-bromo-3-oxo-spiro[3.5]non-1-en-1-ylamino)-3-[4([2,7]naphthyridin-1-ylamino)phenyl]propanoate;

and the salts, solvates, hydrates and N-oxides thereof.

22. A process according to claim 1 for the preparation of:

ethyl (2S)-2-[(2-isopropylsulfanyl-3-oxo-7-oxa-spiro[3.5]non-1-en-1yl)amino]-3-[4-([2,7]naphthyridin-1-ylamino)phenyl]propanoate;

and the salts, solvates, hydrates and N-oxides thereof.

23. A process according to claim 1 for the preparation of:

2-hydroxyethyl (2S)-2-(2-bromo-3-oxo-spiro[3.5]non-1-en-1-ylamino)-3-{4-[(3,5-dichloroisonicotinoyl)amino]phenyl}propanoate;

and the salts, solvates, hydrates and N-oxides thereof.

24. A compound of formula (2):

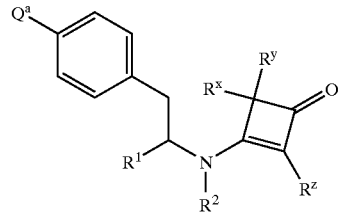

(2)

wherein:

$R^1$ is a carboxylic acid (—$CO_2H$) or an acyclic of cyclic carboxylic acid ester, an amide, tetrazole, phosphonic acid, phosphinic acid, sulphonic acid, sulphinic acid, boronic acid, or an acylsulphonamide group;

$R^2$ is a hydrogen atom or a $C_{1-6}$alkyl group;

$R^x$, $R^y$, and $R^z$, which may be the same or different, are each —$L^1(Alk^1)_n(R^3)_v$, or $R^z$ is —$L^1(Alk^1)_n(R^3)_v$ and $R^x$ and $R^y$ are joined together to form a optionally substituted spiro linked cycloaliphatic or heterocycloaliphatic group;

$L^1$ is a covalent bond or an —O—, —S—, or —Se— atom or an —C(O)—, —C(O)O—, —OC(O)—, —C(S)—, —S(O)—, —S(O)$_2$—, —N($R^8$)—, —CON($R^8$)—, —OC(O)N($R^8$)—, —CSN($R^8$), —N($R^8$)CO—, —N($R^8$)C(O)O—, —N($R^8$)CS—, —S(O)$_2$N($R^8$)—, —N($R^8$)S(O)$_2$—, —N($R^8$)O—, —ON($R^8$)—, —N($R^8$)N($R^8$)—, —N($R^8$)CON($R^8$)—, —N($R^8$)CSN($R^8$)—, or —N($R^8$) SO$_2$N($R^8$)— group;

$R^8$ is a hydrogen atom or an optionally substituted straight or branched $C_{1-6}$alkyl group;

$Alk^1$ is an optionally substituted aliphatic chain or an optionally substituted heteroaliphatic chain containing one to four —O— or —S— atoms or —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— groups that interrupt or are at the terminus of the aliphatic chain;

R$^3$ is a hydrogen or halogen atom or group selected from —OR$^{3a}$ —SR$^{3a}$, —CN and an optionally substituted cycloaliphatic, heterocycloaliphatic, polycycloaliphatic, heteropolycycloaliphatic, aromatic or heteroaromatic group;

R$^{3a}$ is a hydrogen atom or an optionally substituted straight or branched C$_{1-6}$alkyl group or C$_{3-8}$cycloalkyl group;

n is zero or the integer 1; and v is the integer 1, 2 or 3;

provided that when n is zero and L$^1$ is a covalent bond, v is the integer 1;

Q$^a$ is a group —N(R$^4$)H;

R$^4$ is a hydrogen atom or an optionally substituted straight or branched C$_{1-6}$alkyl group;

and the salts, solvates, hydrates and N-oxides thereof.

25. A compound according to claim 24 which is:
3-(4-aminophenyl)-2(S)-(3-oxo-7-oxaspiro[3.5]non-1-en-1-ylamino)propionic acid hydroxyethyl ester.

26. A compound of formula (4):

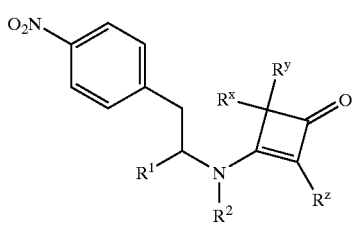

(4)

wherein:

R$^1$ is a carboxylic acid (—CO$_2$H) or an acyclic or cyclic carboxylic acid ester, an amide, tetrazole, phosphonic acid, phosphinic acid, sulphonic acid, sulphinic acid, boronic acid, or an acylsulphonamide group;

R$^2$ is a hydrogen atom or a C$_{1-6}$alkyl group;

R$^x$, R$^y$ and R$^z$, which may be the same or different, are each -L$^1$(Alk$^1$)$_n$(R$^3$)$_v$, or R$^z$ is -L$^1$(Alk$^1$)$_n$(R$^3$)$_y$ and R$^x$ and R$^y$ are joined together to form an optionally substituted spiro linked cycloaliphatic or heterocycloaliphatic group;

L$^1$ is a covalent bond or an —O—, —S—, or —Se— atom or an —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), —N(R$^8$)CO—, —N(R$^8$)C(O)O—, —N(R$^8$)CS—, —S(O)$_2$N(R$^8$)—, —N(R$^8$)S(O)$_2$—, —N(R$^8$, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— group R$^8$ is a hydrogen atom or an optionally substituted straight or branched C$_{1-6}$alkyl group;

Alk$^1$ is an optionally substituted aliphatic chain or an optionally substituted heteroaliphatic chain containing one to four —O— or —S— atoms or —C(O)—, —C(O)O—, —OC(O)—, —C(S)—, —S(O)—, —S(O)$_2$—, —N(R$^8$)—, —CON(R$^8$)—, —OC(O)N(R$^8$)—, —CSN(R$^8$), N(R$^8$)CO—, —N(R$^8$)C(O)O—, N(R$^8$)CS—, —S(O)$_2$N(R$^8$)—, —N(R$^8$)S(O)$_2$—, —N(R$^8$)O—, —ON(R$^8$)—, —N(R$^8$)N(R$^8$)—, —N(R$^8$)CON(R$^8$)—, —N(R$^8$)CSN(R$^8$)—, or —N(R$^8$)SO$_2$N(R$^8$)— groups that interrrupt or are at the terminus of the aliphatic chain;

R$^3$ is a hydrogen or halogen atom or group selected from —OR$^{3a}$, —SR$^{3a}$, —CN and an optionally substituted cycloaliphatic, heterocycloaliphatic, polycycloaliphatic, heteropolycycloaphatic, aromatic or heteroaromatic group;

R$^{3a}$ is a hydrogen atom or an optionally substituted straight or branched C$_{1-6}$alkyl group or C$_{3-8}$cycloalkyl group;

n is zero or the integer 1; and v is the integer 1, 2 or 3;

provided that when n is zero and L$^1$ is a covalent bond, v is the integer 1;

and the salts, solvates, hydrates and N-oxides thereof.

27. A compound according to claim 26 which is:
3-(4-nitrophenyl)-2(S)-(3-oxo-7-oxaspiro[3.5]non-1-en-1-ylamino)propionic acid hydroxyethyl ester.

* * * * *